US009784726B2

(12) United States Patent
Bengtsson

(10) Patent No.: US 9,784,726 B2
(45) Date of Patent: Oct. 10, 2017

(54) SCREENING METHOD, A KIT, A METHOD OF TREATMENT AND A COMPOUND FOR USE IN A METHOD OF TREATMENT

(71) Applicant: ATROGI AB, Stockholm (SE)

(72) Inventor: Tore Bengtsson, Vaxholm (SE)

(73) Assignee: ATROGI AB, Stockholm (SE)

( * ) Notice: Subject to any disclaimer, the term of this patent is extended or adjusted under 35 U.S.C. 154(b) by 0 days.

(21) Appl. No.: 14/759,572

(22) PCT Filed: Jan. 8, 2014

(86) PCT No.: PCT/EP2014/050250
§ 371 (c)(1),
(2) Date: Jul. 7, 2015

(87) PCT Pub. No.: WO2014/108449
PCT Pub. Date: Jul. 17, 2014

(65) Prior Publication Data
US 2016/0003803 A1 Jan. 7, 2016

Related U.S. Application Data

(60) Provisional application No. 61/750,121, filed on Jan. 8, 2013.

(51) Int. Cl.
*G01N 33/50* (2006.01)
*A61K 31/713* (2006.01)
*G01N 33/566* (2006.01)

(52) U.S. Cl.
CPC ....... *G01N 33/5023* (2013.01); *A61K 31/713* (2013.01); *G01N 33/5008* (2013.01); *G01N 33/566* (2013.01)

(58) Field of Classification Search
USPC ... 435/6.1, 14, 91.1, 375, 91.31, 455, 7.1, 1; 424/9.1; 514/1, 2, 44, 1.1; 536/23.1, 536/24.5
See application file for complete search history.

(56) References Cited

U.S. PATENT DOCUMENTS

| 9,657,348 B2 | 5/2017 | Bengtsson |
| 2010/0173928 A1 | 7/2010 | Sabatini et al. |
| 2015/0344958 A1 | 12/2015 | Bengtsson |
| 2017/0016881 A1 | 1/2017 | Bengtsson |
| 2017/0153225 A1 | 6/2017 | Bengtsson |

FOREIGN PATENT DOCUMENTS

| EP | 2426202 A1 | 3/2012 |
| WO | 99/35279 A1 | 7/1999 |
| WO | 99/43326 A1 | 9/1999 |
| WO | 2004/004451 A1 | 1/2004 |
| WO | 2005/013666 A2 | 2/2005 |
| WO | 2005/114195 A1 | 12/2005 |
| WO | 2009/156413 A1 | 12/2009 |
| WO | WO-2016/004995 | 1/2016 |

OTHER PUBLICATIONS

Sarbassov et al, Molecular Cell, vol. 22, pp. 159-168 (2006).*
Bentzinger et al, Cell Metabolism, vol. 8, pp. 411-424 (2008).*
Nave et ai., Biochem. J., 1999, 344, 427-431.
Nedergaard of al., Cell Metab., 2011, 13, 238-240.
Nedergaard et al.., Ann. N. Y. Acad. Sci., 2010, 1212, 20-36.
Nedergaard et al., Am. J. Physiol-Endoc. M., 2007, 293, 444-52.
Nedergaard et al., Biochim. Biophys. Acta., 2005, 1740, 293-304.
Nevzorova et al., Br. J. Pharmacol., 2002, 137, 9-18.
Nevzorova et al., Br. J. Pharmacol., 2006, 147, 446-454.
Ngala et al., Br. J. Pharmacol., 2008, 155, 395-406.
Ngala et al., Br. J. Pharmacol., 2009, 158, 1676-1682.
Nobles et al., Sci. Signal., 2011, 4, RA51.
Nugent et. al. Mol. Endocrinol., 2001, 15, 1729-1738.
Palmada et al., Diabetes, 2006, 55, 421-427.
Phung et al., Cancer Cell, 2006, 10, 159-170.
Ploug et al., Am. J. Physiol., 1987, 253, 12-20.
Polak et al., Cell Metab., 2008, 8, 399-410.
Reinicke et al., J. Cell. Biochem., 2012, 113, 553-562.
Rodnick et al., Diabetes Care, 1992, 15, 1679-1689.
Rowland et al., Traffic, 2011, 12, 672-681.
Santulli et al., Immun Ageing, 2013, 10:10.
Sarabia et al., Biochem. Cell Biol., 1990, 68, 536-542.
Sarbassov et al., Curr. Biol., 2004, 14, 1296-1302.
Sekulic et al., Cancer Res., 2000, 60, 3504-3513.
Shah et al., Int. J. Mol. Sci., 2012, 13, 12629-12655.
Shenoy et al., IJPSR, 2011, 2, 2490-2500.
Shibata et al., Am. J. Physiol., 1989, 257, 96-101.
Shimizu et al., Am. J. Physiol., 1991, 261, 301-304.
Simpson et al., Am. J. Physiol-Endoc. M., 2008, 295, 242-253.
Sobel et al., J. Bacteriol., 1973, 116, 271-278.
Stanford et al., J. Clin. Invest., 2013, 123, 215-223.
Taha et al., The J. Biol. Chem., 1995, 270, 24678-24681.
Taverna et al., Biochim. Biophys. Acts., 1973, 323, 207-219.
Thong et al., Physiology, 2005, 20, 271-284.
Vardanega-Peicher et al., Braz. J. Med. Biol. Res., 2000, 33, 8~5-813.
Violin et al., J. Biol. Chem., 2006, 281, 20577-20588.
Watson-Wright, et al., Muscle Nerve, 1989, 9, 416-422.
Yamamoto et al., Diabetologia, 2007, 50, 158-167.
Zeng et al., Blood, 2007, 109, 3509-3512.
Zierath, Acta. Physiol. Scand. Suppl., 1995, 626, 1-96.
Zinzalla et al., Cell, 2011, 144, 757-768.

(Continued)

*Primary Examiner* — Jane Zara
(74) *Attorney, Agent, or Firm* — McCarter & English, LLP; Steven G. Davis; Mei Bai

(57) ABSTRACT

A method of screening for a candidate compound for the treatment of a condition involving dysregulation of metabolism in a mammal, said method comprising bringing a compound into contact with at least one population of cells, comprising cells that express mTOR and Akt and that are capable of activating mTORC2 and Akt; determining mTORC2 activity and Akt activity in cells brought into contact with the compound, and identifying the candidate compound based on the determined mTORC2 activity and Akt activity. A kit for use in such a method of. A compound for use in a method of treatment of a condition involving dysregulation of metabolism in a mammal, and a method of treatment of such a condition.

8 Claims, 16 Drawing Sheets

(56) References Cited

OTHER PUBLICATIONS

International Search Report and Written Opinion issued in International Application No. PCT/EP2014/050250, mailed Mar. 5, 2014.
Ahren et al., Cell Tissue Res., 1981, 216, 15-30.
Alessi et al., Curr. Biol., 1997, 7, Z61-269
Arch et al., Int. J. Obes., 1996, 20, 191-199.
Barnes et al., J. Cell Sci., 2002, 115, 2433-2442.
Brown et al., Nature, 7 994, 369, 756-758.
Cannon et al., Physiol. Rev., 2004, 84, 277-359.
Carayannopoulos et al., Proc. Nat. Acad. Sci. U.S.A., 2000, 97, 7313-7318.
Chandler et al., Cancer, 2003, 97, 2035-2042.
Chernogubova et al., Endocrinology, 2004, 145, 269-280.
Chernogubova et al., Endocrinology, 2005, 146, 2271-2284.
Copp et al., Cancer Res., 2009, 69, 1821-1827.
Dallner et al., Endocrinology, 2006, 147, 5730-5739.
DeFronzo et al., J. Clin. Invest., 1981, 68, 468-1474.
Dehvari et al., Br. J. Pharmacol., 2012, 165, 1442-1456.
Drake et al., Circ. Res., 2006, 99, 570-582.
Evron et al., Trends Pharmacol. Sci., 2012a, 33, 154-164.
Exton. Diabetes Metab. Rev., 1987, 3, 163-183.
Feldman et aL, PLoS Biol., 2009, 7, 371-383.
Garcia-Martinez et al., Biochem. J., 2009, 421, 29-42.
Gawlik et aL, Mol. Membr. Biol., 2008, 25, 224-235.
Gilman et al., Annu. Rev. Biochem., 1987, 56, 615-649.
Green et al., J. Biol. Chem., 2008, 283, 27653-27667.
Gusovsky, Curr. Protoc. Neurosci., 2001, 7: 7:7.12.1-7.12.11.
Harrison of al., Proc. NatL Acad. Sci. U.S.A., 1991,88, 7839-7843.
Harrison et al., J. Biol. Chem., 1992, 267, 3783-3788.
Hawkins et al., Biochem. Soc. Trans., 2006, 34, 647-662.
Hebert et al., J. Biol. Chem., 1986, 261, 10093-10099.
Hresko et al., J. Biol. Chem., 2005, 280, 40406-40416.
Huang et al., Methods Mol. Biol., 2012, 821, 75-86.
Huang et al., Cell Metab., 2007, 5, 237-252.
Hutchinson et al., Endocrinology, 2005, 146, 901-912.
Hutchinson et al., Diabetes, 2006, 55, 682-690.
Hutchinson et al., Naunyn-Schmiedeberg's Arch. Pharmacol, 2006, 373, 158-168.
Inokuma et al, Diabetes, 2005, 54, 1385-1391.
Jones et al., Exp. Physiol., 2003, 88, 277-284.
Kleiman et al., Biochem. Biophys. Res. Commun., 2009, 388, 554-559.
Koshy et al., J. Vis. Exp., 2010, 45. 10.3791/2429.
Kumar et aL, Diabetes, 2010, 59, 1397-1406.
Lacey et al., Br. J. Pharrnacol, 1991, 103, 1824-1828.
Lamming et al., Cell Metab., 2013, 18, 465-469.
Laplante et al., Cell, 2012, 149, 274-293.
Lawrence et al., Proc. Natl. Acad. Sci. U.S.A., 1992, 89, 3493-3497.
Liggelt et al., Am. J. Physiol., 1988, 254, 795-8.
Liu et al., Am. J. Physiol., 1994, 268, 914-20.
Liu et al., Br. J. Pharmacol., 1996, 117, 1355-1361.
Macaulay et al., Mol. Cell. Biochem., 1994, 141, 27-33.
Macheda et al., J. Cell. Physio., 2005, 202, 654-662.
Marette et al., Am. J. Physiol., 1989. 257, 714-21.
Murata et al., AIDS, 2002, 16, 859-863.
Bryant et al., Regulated transport of the glucose transporter GLUT4. Nat Rev Mol Cell Biol. Apr. 2002;(4):267-77.
Gaster et al., GLUT4 is reduced in slow muscle fibers of type 2 diabetic patients: is insulin resistance in type 2 diabetes a slow, type 1 fiber disease? Diabetes. Jun. 2001;50(6):1324-9.
Kovala et al., Protein kinase A regulation of cAMP phosphodiesterase expression in rat skeletal myoblasts. J Biol Chem. Mar 25, 1994;269(12):8680-5.
Neve et al., Turnover of beta 1— and beta 2-adrenergic receptors after down-regulation or irreversible blockade. Mol Pharmacol. Aug. 1986;30(2):104-11.
Shan et al., Effects of GLUT4 expression on insulin resistance in patients with advanced liver cirrhosis. J Zhejiang Univ Sci B. Aug. 2011;12(8):677-82.
Sprenger et al., Biophysical techniques for detection of cAMP and cGMP in living cells. Int J Mol Sci. Apr. 12, 2013;14(4):8025-46.

* cited by examiner

A

B

SCREENING METHOD, A KIT, A METHOD OF TREATMENT AND A COMPOUND FOR USE IN A METHOD OF TREATMENT

CROSS-REFERENCE TO RELATED APPLICATIONS

This application is a 35 U.S.C. §371 national stage filing of International Application No. PCT/EP2014/050250, filed on Jan. 8, 2014, which claims the benefit of U.S. Provisional Application No. 61/750,121, files on Jan. 8, 2013. Each of the foregoing applications is incorporated herein by reference in its entirety.

FIELD OF THE INVENTION

The present invention relates to a screening method, in particular to a method of screening for a compound for the treatment of a condition involving a dysregulation of metabolism in a mammal, such as a dysregulation of glucose homeostasis or glucose uptake, as well as to a kit for use in such a method. The invention also relates to a compound for use in such treatment, a pharmaceutical composition comprising the compound, and a method of treatment of such a condition.

BACKGROUND OF THE INVENTION

Following a meal, increased blood glucose levels stimulate insulin release from the pancreas to act throughout the body to lower blood glucose levels. Important sites of action of insulin on glucose metabolism include facilitation of glucose uptake into skeletal muscle and adipocytes, and an increase of glycogen storage in the liver. Skeletal muscle and adipocytes is responsible for insulin-mediated glucose uptake and utilization in the fed state, making them very important sites for glucose metabolism.

Diabetes comprises two distinct diseases, viz. type 1 (or insulin-dependent diabetes) and type 2 (insulin-independent diabetes), both of which involve the malfunction of glucose homeostasis. Type 2 diabetes affects more than 350 million people in the world and the number is rising rapidly. Complications of diabetes include severe cardiovascular problems, kidney failure, peripheral neuropathy, blindness and even loss of limbs and death in the later stages of the disease. Type 2 diabetes is characterized by insulin resistance in skeletal muscle and adipose tissue (fat), and at present there is no definitive treatment. Most treatments used today are focused on treating dysfunctional insulin signaling or inhibiting glucose output from the liver and many of those treatments have several drawbacks and side effects. There is thus a great interest in identifying novel insulin-independent ways to treat different form of metabolic orders connected with dysregulation of glucose uptake such as type 2 diabetes.

In type 2 diabetes the insulin-signaling pathway is blunted in peripheral tissues such as fat and skeletal muscle. Methods for treating type 2 diabetes typically include lifestyle changes, as well as the administration of insulin or oral medications to help the body with the glucose homeostasis. People with type 2 diabetes in the later stages of the disease develop "beta-cell failure" or the inability of the pancreas to release insulin in response to high blood glucose levels. In the later stages of the disease patients often require insulin injections, in combination with oral medications, to manage their diabetes. In type 2 diabetes the insulin-signaling pathway is blunted in peripheral tissues and most common drugs have side effects including the said down regulation or desensitization of the insulin pathway and/or the promotion of fat incorporation in fat, liver and skeletal muscle, furthermore increased stimulation of proliferation of certain cells and a higher risk of promoting cancer. There is thus a great interest in identifying novel ways to treat metabolic diseases including type 2 diabetes that do not include these side-effects.

The molecular understanding of the signaling pathway below the insulin receptor has been a very hard problem to solve and has been occupying a great number of researchers since the discovery of insulin. In short, control of glucose uptake by insulin involves activation of the insulin receptor (IR), insulin receptor substrate (IRS), phosphoinositide 3-kinase (PI3K) and thus stimulation of phosphatidylinositol (3,4,5)-triphosphate (PIP3), mammalian target of rapamycin also called mechanistic target of rapamycin (mTOR), Akt/PKB (Akt) and TBC1D4 (AS160), leading to translocation of glucose transporter 4 (GLUT4). Akt activation is considered necessary for GLUT4 translocation.

Akt has multiple actions and regulates cellular metabolism and survival. Akt can promote cell survival both directly and indirectly. Akt can promote proliferation and differentiation and has impact on the cell cycle and migration of cells. Akt can influence transcription and translation. Akt has been implicated in angiogenesis and tumor growth. Thus Akt promotes changes in cells and tissues that can lead to cancer and other pathophysiological effects, such as obesity and negative effects on insulin signaling. It would thus be desirable to be able to increase glucose uptake without stimulating Akt to circumvent these side-effects.

Another important protein involved in the insulin-signaling pathway is mTOR. mTOR is regulated by several upstream pathways involved in energy uptake of the cell. mTOR is a complex that exists in two complexes: mTOR complex-1 (mTORC1), which includes the protein raptor, and mTOR complex-2 (mTORC2), which includes the protein rictor. PI3K has a key function upstream of mTOR in the insulin pathway by generating polyphosphoinositides in the plasma membrane, which function as a docking site for Akt. Thereby Akt is brought close to its activating kinases; PDK-1, which phosphorylates Akt on Thr308, and mTORC2, which phosphorylates Akt on Ser473 (Rowland, Fazakerley & James 2011).

Insulin and catecholamines are released in the body in response to quite different stimuli. Whereas insulin is released in response to the rise in blood sugar levels after a meal, epinephrine (also referred to as adrenaline) and norepinephrine (also referred to as noradrenaline) are released due to various internal and external stimuli, such as exercise, emotions and stress but also homeostatic tissue regulation. Insulin is an anabolic hormone that stimulates many processes involved in growth including glucose uptake, glycogen and triglyceride formation whereas catecholamines are mainly catabolic. Although insulin and catecholamines normally have antagonistic effects, it has been shown previously that they have similar actions in skeletal muscle on glucose uptake (Nevzorova et al. 2006). It is likely that catecholamines stimulate glucose uptake via adrenergic receptors to supply muscle cells with an energy substrate. Thus, it is likely that in mammals, including humans, the adrenergic and insulin systems can work independently to provide for the energy need of skeletal muscle during different situations. Since insulin stimulates many anabolic processes including a number of unwanted side effects it would be beneficial to be able to stimulate glucose uptake through the newly found adrenergic signaling pathway, which is catabolic and does not include many of the unwanted processes.

It is known in the field of the art that adrenergic receptors are prototypic models for the study of G protein-coupled receptors (GPCRs) and their signaling (Santulli, Iaccarino 2013, Drake, Shenoy & Lefkowitz 2006). There are three different classes of ARs, with distinct expression patterns and pharmacological profiles: $\alpha_1$-, $\alpha_2$- and $\beta$-ARs. The $\alpha_1$-Ars comprise the $\alpha_{1A}$, $\alpha_{1B}$ and $\alpha_{1D}$ while $\alpha_2$-ARs are divided into $\alpha_{2A}$, $\alpha_{2B}$ and $\alpha_{2C}$. The $\beta$-ARs are also divided into the subtypes $\beta_1$, $\beta_2$, and $\beta_3$, of which $\beta_2$-AR is the major isoform in skeletal muscle cells (Watson-Wright, Wilkinson 1986, Liggett, Shah & Cryer 1988). Adrenergic receptors are G protein coupled and signal through second messengers such as cAMP and phospholipase C and are thus suited as prototypical models for most classes of GPCRs.

Glucose uptake in cells is mainly considered to be through facilitative glucose transporters (GLUT). GLUTs are transporter proteins mediating transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied iso forms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in e.g. brain, kidney, and liver. GLUT4 is the major iso form involved in insulin stimulated glucose uptake.

To treat a condition involving a dysregulation of glucose homeostasis or glucose uptake in a mammal, it would be very advantageous to be able to activate certain GLUTs. For example for diseases such as type 2 diabetes it is vital to activate GLUT4 translocation to the plasma membrane and thus glucose uptake. Regulation of GLUT1 translocation or intrinsic activity has been suggested to occur in several tissues including erythrocytes depending on ATP-levels (Hebert, Carruthers 1986). It has also been indicated in HEK-cells (Palmada et al. 2006), 3T3-L1 (Harrison et al. 1992) and clone-9 cells (Barnes et al. 2002). Impaired GLUT translocation, of in particular GLUTS, has been reported as involved in both male and female infertility (Gawlik et al. 2008, Carayannopoulos et al. 2000). The mechanism whereby insulin signaling increases glucose uptake is mainly via GLUT4-translocation from intracellular storage to the plasma membrane (Rodnick et al. 1992). After longer insulin stimulation also GLUT1-content is increased due to increased transcription (Taha et al. 1995). Glucose uptake in type 2 diabetes is associated with defects in PI3K activity, insulin receptor tyrosine, IRS and Akt phosphorylation, resulting in impairment of GLUT4 translocation to the plasma membrane. Impaired GLUT translocation also plays a role in muscle wasting. Furthermore, GLUT translocation plays a role in feeding behavior. Mice lacking GLUT4 develop problems with lipid and glucose homeostasis leading to changes in feeding behavior. Decreased concentrations of GLUT1 and GLUT3 have also been shown in the brains of patients with Alzheimer's disease (Simpson et al. 2008). Also in a review article of Shah K, et al. (Shah, Desilva & Abbruscato 2012) the role of glucose transporters in brain disease, diabetes and Alzheimer's disease is discussed.

SUMMARY OF THE INVENTION

It has been surprisingly found that mTOR, in the form of mTORC2, can be stimulated to increase glucose uptake without substantially stimulating Akt. Drugs that stimulate mTORC2 can thus be used to treat metabolic disorders, in particular related to dysregulation of glucose transport including insulin resistance or hyperglycemia, type 2 diabetes, inadequate glucose tolerance, obesity, polycystic ovary syndrome (PCOS), hypertension and the metabolic syndrome It further has been surprisingly found that there are GPCRs ligands that, by acting on GPCRs, can increase glucose uptake in skeletal muscle. Indeed, experiments in GK rats that are a model for type 2 diabetes reveal that it is possible to improve glucose tolerance in a glucose tolerance test via GPCRs.

A key concept of the present invention therefore pertains to the ability of GPCRs to increase cellular effects such as glucose uptake through mTORC2 without stimulating Akt in cells. The glucose uptake can be through GLUT selected from any of the fourteen members of the GLUT1-14 but preferably through GLUT1 or GLUT4, in particular GLUT4. The cells are any mammalian cells that express GLUT, but preferably cells expressing GLUT1 or GLUT4, in particular GLUT4.

A major problem with obesity and type 2 diabetes is that peripheral tissues become insulin resistant and glucose uptake is blunted. According to the present invention, this can be treated with compounds that stimulate mTORC2 and upregulate glucose uptake in peripheral tissues. Upregulating glucose uptake via compounds that stimulate mTORC2 without stimulating Akt reduces requirement of insulin or insulin mimetic drugs. Accordingly, the incidence of life threating complications of obesity and type 2 diabetes can be reduced. Such approach could also be therapeutically useful in other human diseases that are induced by, regulated by, or associated with, changes in glucose homeostasis.

Consequently, a first aspect is method of screening for a candidate compound for the treatment of a condition involving dysregulation of metabolism in a mammal, said method comprising:
  bringing a compound into contact with at least one population of cells, comprising cells that express mTOR and Akt and that are capable of activating mTORC2 and Akt;
  determining mTORC2 activity and Akt activity in cells brought into contact with the compound, and
  identifying the candidate compound based on the determined mTORC2 activity and Akt activity.

In some embodiments, the candidate compound is identified as a compound that causes an increase in activity of mTORC2 without causing an increase in activity of Akt.

For example, the candidate compound may be identified by comparing mTORC2 activities and Akt activities determined in cells that have been brought into contact with the compound, with mTORC2 and Akt activities determined in similar cells that have not been brought into contact with the compound.

In other embodiments, the candidate compound is identified, as a compound that causes an increase in activity of mTORC2 but that causes an increase in activity of Akt that is less than a selected reference value.

In such embodiments, the Akt activities determined in cells brought into contact with the compound may be compared with Akt activities determined in cells brought into contact with a known Akt agonist, such as insulin.

The effect of the contacting, on the activation of mTORC2 in the cells, e.g. may be determined by measuring phosphorylation of mTORC2, e.g. on Ser2481; while the effect of the contacting on the activity of Akt in the cells e.g. may be determined by measuring phosphorylation of Akt, e.g. on Ser473.

In some embodiments, the cells that express mTOR further express a GPCR, e.g. an adrenergic receptor. In some embodiments, the adrenergic receptor is a beta-adrenergic receptor. In other embodiments, the adrenergic receptor is an alpha-adrenergic receptor.

In some embodiments, the cells that express mTOR (and optionally also express a GPCR) further express a GLUT, e.g. GLUT1, GLUT3 or GLUT4, in particular GLUT4. In such embodiments, the effect of the contacting, on the activity of mTORC2 in the cells may be determined by detecting the presence of GLUT in the cell membrane of the cells and/or by detecting glucose uptake in the cells.

The cells that express mTOR preferably are mammalian cells, selected from muscle cells, e.g. skeletal muscle cells, heart cells, adipocytes, such as brown fat cells and white fat cells, beta cells, brain cells, liver cells, reproductive cells and cells involved in reproduction, and mammary cells.

The condition involving a dysregulation of metabolism in a mammal e.g. may be a condition involving a dysregulation of glucose homeostasis or glucose uptake, such as Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, and vascular disease.

Another aspect is a kit for use in a method of the invention, said kit comprising cells capable of expressing mTOR and Akt, together with instructions for use of the kit.

In some embodiments, the kit comprises cells capable of expressing mTOR and a GPCR, such as an adrenergic receptor.

In some embodiments, the kit comprises cells capable of expressing mTOR and a GLUT, e.g. GLUT1, GLUT3 or GLUT4.

Cells provided in the kit of the present invention preferably are mammalian cells, such as cells selected from skeletal muscle cells, heart cells, adipocytes, such as brown fat cells and white fat cells, beta cells, brain cells, liver cells, reproductive cells and cells involved in reproduction, and mammary cells.

One further aspect is a compound for use in a method of treatment or prevention of a condition involving a dysregulation of metabolism in a mammal, by administering, to a mammal in need of such treatment or prevention, a therapeutically effective amount of a compound which is an activator of mTORC2 in at least some cells of the mammal, but which compound does not cause an increase of Akt activation in cells of the mammal.

Still a further aspect is method of treatment or prevention of a condition involving a dysregulation of metabolism in a mammal, by administering, to a mammal in need of such treatment or prevention, a therapeutically effective amount of a compound which is an activator of mTORC2 in a cell of the mammal, but which compound does not cause an increase of Akt activation in said cells.

BRIEF DESCRIPTION OF THE DRAWINGS

FIG. 1 illustrates that activating prototypic GPCRs may lead to stimulated glucose uptake in a cell.

FIG. 2 illustrates that activating prototypic GPCRs leads to stimulated glucose uptake in skeletal muscle cells.

FIG. 3 illustrates that PIP3 is not produced by activating prototypic GPCRs.

FIG. 4 illustrates that Akt is involved in insulin stimulated glucose uptake but not in GPCR activated glucose uptake.

FIG. 5 illustrates that phosphorylation of Akt is not involved in GPCR stimulated glucose uptake.

FIG. 6 illustrates that activating a number of GPCR does not stimulate Akt phosphorylation as insulin does.

FIG. 7 illustrates that phosphorylation of AS-160 is not involved GPCR stimulated glucose uptake.

FIG. 8 illustrates that Akt phosphorylation is not affected by GPCR stimulation and that PDK1 inhibition significantly inhibits insulin-mediated T308-Akt phosphorylation but has no effect on S473-Akt phosphorylation.

FIG. 9 illustrates that Akt phosphorylation is not affected by GPCR stimulation and that mTOR inhibition significantly inhibits insulin-mediated S473-Akt phosphorylation but has no effect on T308-Akt phosphorylation.

FIG. 10 illustrates that mTOR inhibition significantly inhibits insulin and GPCR stimulated glucose-uptake in L6 myotubes and CHO GLUT4 cells.

FIG. 11 illustrates that the mTOR inhibitor KU0063794 inhibits insulin and GPCR stimulated glucose-uptake in intact soleus muscle ex-vivo.

FIG. 12 illustrates that the mTOR inhibitor KU0063794 inhibits insulin and GPCR stimulated glucose-uptake in skeletal muscle in-vivo.

FIG. 13 illustrates that insulin treatment causes robust phosphorylation of mTOR at both S2448 and S2481, whereas isoproterenol phosphorylates mTOR only at S2481.

FIG. 14 illustrates that mTORC1 inhibition has no effect on either insulin or GPCR stimulated glucose uptake.

FIG. 15 illustrates that mTORC2 inhibition significantly inhibits both insulin and GPCR stimulated glucose uptake.

FIG. 16 illustrates that efficient knock-down of Raptor fails to affect either insulin or isoproterenol-stimulated glucose uptake, whereas knock-down of Rictor significantly inhibits both insulin- and GPCR-stimulated glucose-uptake.

FIG. 19 illustrates that GPCR-stimulated glucose uptake involves GLUTs.

FIG. 20 illustrates that mTOR inhibition significantly inhibits insulin and GPCR stimulated GLUT4 translocation in L6 myotubes.

DETAILED DESCRIPTION OF THE INVENTION

Figure 1:
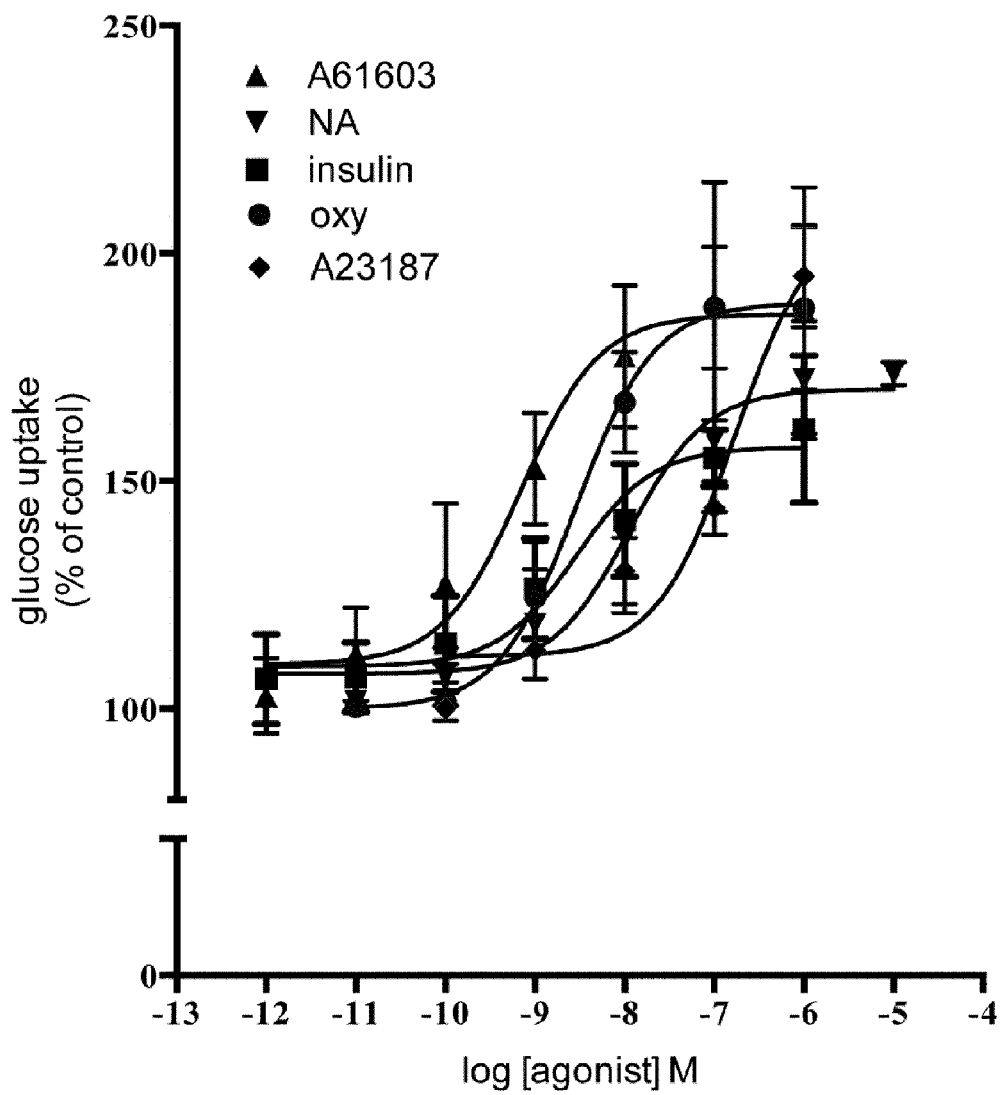
FIG. 1 is a semi-logarithmic graph showing glucose uptake (% of control) in CHO GLUT4 cells brought into contact with different concentrations of the compounds A61603, noradrenaline (NA), insulin, oxymetazoline (oxy), and A23187.

By GPCR ligand is meant any molecule capable of binding a GPCR. The GPCR ligand can be selected from known or unknown GPCR ligands and agonists. Ligand denotes here any molecule binding to the receptor.

A compound that either binds GPCR directly or acts by stabilizing the GPCR is referred to as a ligand for GPCR.

By a condition involving a dysregulation of metabolism in a mammal, e.g. a condition involving a dysregulation of glucose homeostasis or glucose uptake, is meant a condition, disease or disorder induced by, regulated by, or associated with a dysregulation metabolism, in particular of glucose homeostasis or glucose uptake. Such a condition may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, vascular disease, etc.

It should be realized that even when identified as a "candidate compound for the treatment of a condition involving dysregulation of metabolism in a mammal", the compound may have to pass various other tests, e.g. pharmacological, clinical and toxicological tests so on, before being able to be used as a drug. Thus, the expression "candidate compound for the treatment of a condition involving dysregulation of metabolism in a mammal" should not be generally construed as a statement that the method permits to positively identify a compound for use in such a treatment, but rather should be understood as an indication that the method permits to identify a compound that may have a usefulness in such treatment.

The word "cell" when used herein, generally refers to a population of cells, and not to one single cell, unless the contrary is specified or apparent from the context.

By GLUT is meant any of the 14 mammalian glucose transporter proteins, GLUT1-14.Reference to "GLUT" in singular does not mean one GLUT only, unless apparent from the context or otherwise specified, but should be construes as reference to a plurality of mammalian glucose transporter proteins. Preferably the GLUT is a GLUT belonging to class I, in particular GLUT1, GLUT3 or GLUT4, preferably GLUT1 or GLUT4, most preferably GLUT4.

By "translocation" of GLUT is meant the "migration" of GLUT from the interior of the cell to the cell membrane.

A mammal is any mammal including humans, laboratory animals, domestic pets and farm animals. Preferably, the mammal is a human.

The protein mTOR exists in combination with raptor as mTOR complex 1 (mTORC1) and with rictor as mTOR complex 2 (mTORC2) (Alessi et al. 1997). The term mTOR as used herein generally refers equally to mTOR when present as mTORC1 and as mTORC2, unless the contrary is specified or apparent from the context.

As used herein, "a cell expressing mTOR" or "cells expressing mTOR", or "cells that express mTOR", etc. generally refer to cells that are also able to activate at least mTORC2, unless the contrary is apparent from the context or indicated.

"A cell expressing Akt" or "cells expressing Akt", or "cells that express Akt", etc. generally refer to cells that are also able to activate Akt, unless the contrary is apparent from the context or indicated.

"A cell expressing GLUT" or "cells expressing GLUT", or "cells that express GLUT", etc. generally refer to cells that are also able to translocate GLUT, unless the contrary is apparent from the context or indicated.

In a first aspect the present invention relates to a method of screening for a candidate compound for the treatment of a condition involving dysregulation of metabolism in a mammal, said method comprising:
bringing a compound into contact with at least one population of cells, comprising cells that express mTOR and Akt and that are capable of activating mTORC2 and Akt;

determining mTORC2 activity and Akt activity in cells brought into contact with the compound, and
identifying the candidate compound based on the determined mTORC2 activity and Akt activity.
In some embodiments, the method comprises:
bringing the compound into contact with cells that express mTOR, said cells being capable of activating mTORC2, and
determining the activity of mTORC2 in said cells;
bringing the compound into contact with cells that express mTOR, which cell further express Akt, and that are capable of activating mTORC2 and Akt; and
determining the activity of Akt in said cells; and
identifying the candidate compound based on the determined mTORC2 activity and Akt activity.

In some embodiments, the present invention relates to a method of screening for a candidate compound for the treatment of a condition involving dysregulation of metabolism in a mammal, said method comprising:
bringing a compound into contact with at least one population of cells, comprising cells that express mTOR, a GLUT and Akt and that are capable of activating mTORC2 and Akt;
determining GLUT translocation and Akt activity in cells brought into contact with the compound, and
identifying the candidate compound based on the determined GLUT translocation and Akt activity.
In some embodiments, the method comprises
providing cells that express mTOR and at least one GLUT,
contacting the cells with the compound, and
determining GLUT translocation in the cells;
providing cells that express mTOR and Akt,
contacting the cells with the compound, and
determining Akt activity in the cells; and
identifying the candidate compound based on the determined GLUT translocation and Akt activity.

The GLUT translocation in the cells may be determined, e.g. by measuring the uptake of a hexose, such as glucose, into the cells.

Thus, some embodiments, the present invention relates to a method of screening for a candidate compound for the treatment of a condition involving dysregulation of metabolism in a mammal, said method comprising:
bringing a compound into contact with at least one population of cells, comprising cells that express mTOR, a GLUT and Akt and that are capable of activating mTORC2 and Akt;
determining hexose uptake, e.g. glucose uptake, and Akt activity in cells brought into contact with the compound, and
identifying the candidate compound based on the determined hexose uptake, and Akt activity.
In some embodiments, the screening method comprises
providing cells that express mTOR and at least one GLUT,
contacting the cells with the compound,
determining uptake of a hexose, such as glucose, into the cell;
providing cells that express mTOR and Akt,
contacting the cells with the compound, and
determining Akt activity in the cell; and
identifying the candidate compound based on the determined hexose uptake and Akt activity.
In some embodiments, the cells expressing mTOR and at least one GLUT are different from the cells expressing mTOR and Akt.

In some embodiments, the cells expressing mTOR and at least one GLUT, are the same as the cells expressing mTOR and Akt.

In some embodiments, each cell used in the screening method expresses mTOR, as well as a GLUT and Akt.

mTORC2 may be activated in response to a signal from a GPCR. Therefore, in some embodiments, the cells that express mTOR also express a GPCR.

Adrenergic receptors are considered prototypical for GPCRs and have been investigated extensively (Santulli, Iaccarino 2013, Drake, Shenoy & Lefkowitz 2006). In some embodiments, therefore, the GPCR is an adrenergic receptor (AR). In some particular embodiments, the GPCR is an alpha-AR. In some embodiments, the GPCR is an $\alpha_1$-AR. In some other embodiments, the GPCR is an $\alpha_2$-AR. In still other embodiments, the GPCR is a β-AR. In some embodiments, the GPCR is a $\beta_1$-AR. In other embodiments, the GPCR is $\beta_2$-AR. In other embodiments, the GPCR is a $\beta_3$-AR As noted herein, a condition involving a dysregulation of metabolism, in particular is selected from conditions involving a dysregulation of glucose homeostasis or glucose uptake in a mammal. Such conditions may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility, infertility, retinopathy, stroke, vascular disease, etc.

In some embodiments, such the condition is selected from metabolic syndrome, obesity, and diabetes, e.g. type 1 diabetes or type 2 diabetes. In some other embodiments, the condition is selected from type 1 diabetes and type 2 diabetes, in particular type 2 diabetes.

In one aspect, the present invention relates to a method for the screening of a candidate compound for use in any of the above-mentioned methods of treatment. Thus, one aspect relates to methods for screening compounds that increase GLUT translocation in cells, including skeletal muscle cells, heart cells, brown fat cells, white fat cells, beta cells, brain cells, liver cells, reproductive cells and cells involved in reproduction, mammary cells, and essentially any cells of the body where beta- adrenergic receptors and GLUT are expressed.

According to one aspect, the invention provides a method for identifying GPCR ligands that do not activate Akt but that stimulate GLUT translocation to the plasma membrane and glucose uptake, and which therefore will provide for a treatment for any condition involving a dysregulation of glucose homeostasis or glucose uptake in a mammal.

An increase in GLUT translocation may be measured e.g. by measuring an increase in uptake of a hexose, such as fructose or glucose, in particular glucose, into the cell.

Depending on the disorder that it is desired to treat, the GLUT is selected from any of GLUT1-14, preferably from any GLUT within class I.

For example, in one embodiment, the screening method of the invention is directed to identifying a compound useful in the treatment of diabetes, e.g. type 2 diabetes, and the GLUT preferably is GLUT1 or GLUT4, more preferably GLUT4.

In another embodiment, the screening method of the invention is directed to identifying a compound useful in the treatment of a neurodegenerative disorder, and the GLUT is selected from GLUT1, GLUT3 and GLUT4, in particular GLUT1

In another embodiment, the screening method of the invention is directed to identifying a compound useful in the treatment of male or female infertility, and the GLUT is preferably GLUT8.

In another embodiment, the screening method of the invention is used to determine whether known drugs already in use for treating other diseases also activate mTORC2 without stimulating Akt. This would reveal new mechanisms of action for old drugs that might provide for a novel medical use of the drug in conditions involving dysregulation of metabolism in a mammal, e.g. diseases caused by or associated with failure of glucose uptake and GLUT translocation, such as insulin resistance, obesity, diabetes and complications resulting from these disorders.

In some embodiments, the screening method may include a preliminary screening of substances to identify compounds that bind to GPCRs, i.e. compounds that are GPCR ligands. Such preliminary identification of ligands for GPCRs may be accomplished using e.g. in silico methods or methods using preparations of plasma membrane from tissue. In such a preliminary screening, a cell free assay system based on protein-protein interaction can also be used, such as one using electrochemiluminiscence.

Thus, by use of cell-free methods, compounds that bind GPCRs can be identified in a preliminary screening step. Preferable molecules identified in such a method are small molecules with a molecular weight less than or equal to 1000 Daltons. These compounds are then screened in the cell-based screening method as described herein.

The screening method according to the present invention is not limited to any particular compounds, i.e. the compound may be any pharmaceutically acceptable substance, e.g. a known pharmaceutical substance.

In one embodiment, compounds that are previously known GPCR ligands can be screened in the method of the invention, in order to identify such GPCR ligands that cause an increase in mTORC2 activity and glucose uptake and GLUT translocation without activating Akt.

A preferable compound for screening in the method of the invention is one that may be administered orally in order to enhance glucose uptake in peripheral tissues.

A suitable cell for use in the screening method of the invention may be derived e.g. from primary cultures from heart, skeletal muscle, brown fat, white fat, brite/beige fat, liver, brain, mammal gland and other mammalian tissues. The cell or cells to be used in the screening method generally is selected so as to be representative of the tissue(s) involved or afflicted by the condition, disease or disorder. For example, if the screening method is directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the screening method is directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be utilized include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with GPCRs and/or GLUT can also be used. Although a number of cell types can be used for this process, one that can be transfected and express (or overexpress) GPCRs and/or GLUT would be preferable, for example CHO cells. The introduced GPCR and/or GLUT could be stably transfected or non-stably transfected according to methods well known to investigators of skill in the art.

In the screening method of the invention, the Akt activity may be determined by measuring any parameter $P_{Akt}$ which is a measurable parameter that may be considered representative for the Akt activity. For example, $P_{Akt}$ may be the activity of Akt in the cell, or the activity of any target molecule downstream of Akt, which in some circumstances can be measured as a phosphorylation product. For example, phosphorylation of Akt, e.g. on Ser473, or of a target molecule downstream of Akt may be used as a parameter representative of the activity of Akt.

The activity of Akt may be determined by detecting phosphorylated AS 160, as described in Example 1.

There also are numerous commercial kits available for measuring Akt activity. For example, Akt Kinase Assay Kit (Nonradioactive) #9840, permits to measure Akt kinase activity in the cell. In this assay, immobilized Akt (1G1) mAb is used to immunoprecipitate Akt from cell extracts and an in vitro kinase assay is performed using GSK-3 Fusion Protein as a substrate. Phosphorylation of GSK-3 is measured by Western blotting, using Phospho-GSK-3alpha/beta (Ser21/9) Antibody. Another kit useful for determining Akt activity is Phospho-AKT (Ser473) & Phospho-Akt (Thr308) Cellular Assay Kit from Cisbio Bioassays, permitting to detect activated Akt when phosphorylated either at Ser 473 or at Thr 308 directly in whole cells. These assays are based on sandwich immunoassays, each involving two monoclonal antibodies: the anti-phospho-AKT antibody labeled with Eu3+-cryptate and the anti-Akt antibody labeled with d2.

The activity of mTORC2 may be determined e.g. by measuring the kinase activity of mTORC2, e.g. using an in vitro assay as described by Huang J. in Methods Mol Biol. 2012; 821:75-86.

Since mTORC2 is activated by phosphorylation of mTOR, the activity of mTORC2 also may be determined by measuring phosphorylation of mTOR, in particular phosphorylation of 52448 and/or 52481 of mTOR, especially phosphorylation of 52481.

Activation of mTORC2 results in enhanced GLUT translocation in a cell expressing a GLUT. Therefore the activity of mTORC2 also may be determined by determining GLUT translocation in a cell expressing a GLUT. The GLUT translocation may be determined by measuring any parameter $P_{GLUT}$ which is a measurable parameter that may be considered representative for the translocation of a GLUT in the cell. For example, $P_{GLUT}$ may be e.g. the uptake of a hexose, such as fructose or glucose, of the cell, in particular the uptake of glucose, or the presence of the GLUT in the cell membrane. The GLUT may be selected from any one of the GLUT 1-14, e.g. GLUT1 and GLUT4, in particular GLUT4. $P_{GLUT}$ also may be the GLUT translocation, e.g. measured by use of a method as described in (Koshy et al. 2010).

In some embodiments of a screening method according to the invention, the cells are grown in a cell culture medium, transferred into a sample well of a conventional microplate having e.g. 8, 12, 24, 48, 96, 384 or 1536 sample wells, cell differentiation is induced by addition of a differentiation medium, and the cells are allowed to differentiate for a suitable time period. The cells are then brought into contact with the compound for a predetermined time period, of e.g. 5 minutes to 10 hours, or 0.5 hour to 5 hours, e.g. 1 hour to 3 hours.

The compound generally is provided dissolved in a liquid phase, which e.g. may be an aqueous phase, such as purified water or a suitably buffered and isotonic aqueous phase, or an organic solvent phase, or a mixture thereof. The compound is brought into contact with the cells at a concentration that suitably should correspond to an amount relevant for pharmaceutical use, e.g. a concentration of $10^{-8}$ to $10^{-1}$ M, or $10^{-7}$ to $10^{-2}$ M, e.g. $10^{-6}$ to $10^{-3}$ M.

The candidate compound is identified based on the determined mTORC2 activity and Akt activity in cells brought into contact with the compound to be screened. Preferably, the screening method involves comparing mTORC2 and Akt activities determined in cells brought into contact with the compound, with reference values.

Thus, in some embodiments, the activity of mTORC2 determined in a cell brought into contact with a compound ($mTORC2_{comp}$) is compared to the activity of mTORC2 ($mTORC2_{ref}$), determined for a similar cell which has not been brought into contact with the compound, such as a cell treated with buffer only under similar conditions. In such case, for the compound be contemplated as a candidate compound, invention, $mTORC2_{comp}$ should be higher than $mTORC2_{ref}$.

The reference value also may be the mTORC2 activity obtained when bringing cells expressing mTOR into contact with a compound having a determined or previously known mTORC2 activating capacity, such as isoproterenol. Thus, in some embodiments, the activity of mTORC2 determined for cells brought into contact with a compound to be screened ($mTORC2_{comp}$) is compared to the mTORC2 activity ($mTORC2_{agonist}$), determined for similar cells brought into contact with a compound of a known mTORC2 activating effect, such as isoproterenol.

Similarly, in some embodiments, the activity of Akt determined in cells brought into contact with a compound to be screened ($Akt_{comp}$) is compared a suitable reference Akt activity ($Akt_{ref}$), determined in similar cells that have not been brought into contact with the compound, such as cells treated with buffer only under similar conditions.

In some other embodiments, the activity of Akt determined in cells brought into contact with a compound to be screened ($Akt_{comp}$) is compared a suitable reference Akt activity ($Akt_{ref}$), determined in similar cells brought into contact a compound, having a previously determined or known Akt activating capacity, such as insulin.

Based on the above determinations, the screening method permits to identify, as a candidate compound, a compound that causes an increase in activity of mTORC2 without causing an increase in activity of Akt or causing an increase in activity of Akt that is considered acceptable, as will be discussed herein below. Indeed, it should be realized that a minor increase in Akt activity in some cases may be tolerated.

In some embodiments, in order to identify a candidate compound a difference $\Delta_1$ between $Akt_{comp}$ and $Akt_{ref}$ is calculated and should be as close to 0 as possible. For example, in order for a compound to be considered as not causing an increase of the Act activity, a ratio r $$r = \frac{Aktcomp - Aktref}{Aktref}$$

may be calculated and a limit may be selected below which the compound is considered as not causing any increase in the Akt activity. For example, a compound having a ratio r lower than 0.7, or lower than 0.5, or lower than 0.4, or lower than 0.3, or lower than 0.2, e.g. lower than 0.15, or lower than 0.1, may be contemplated as a candidate compound.

In some embodiments, the method also comprises measuring the Akt activity ($Akt_{agonist}$) obtained in similar cells brought into contact with an agonist, e.g. insulin, known to elicit an increase of Akt activity. A difference $\Delta_2$ between $Akt_{agonist}$ and $Akt_{comp}$ may then be calculated. A ratio r'

$$r' = \frac{Akt agonist - Akt comp}{Akt agonist}$$

may then be calculated. For example, a compound having a ratio r' higher than 0.1, or higher than 0.2, or higher than 0.3, or higher than 0.4, or higher than 0.5, or higher than 0.6, or higher than 0.7, e.g. higher than 0.8, or higher than 0.9, may be contemplated as a candidate compound.

As an alternative, Akt activity may be determined in cells brought into contact with the compound to be screened, and in similar cells brought into contact with a known Akt agonist, as well as in cells not brought into contact with either compound to be screened or the Akt agonist, and a ratio r"

$$r'' = \frac{Akt comp - Akt ref}{Act agonist - Akt ref}$$

may be calculated. Thus, in some embodiments, a compound having a ratio r" lower than 0.7, or lower than 0.5, or lower than 0.4, or lower than 0.3, or lower than 0.2, e.g. lower than 0.1, may be contemplated as a candidate compound.

In some embodiments, in order to calculate r, r' or r", the activity values are indicated as a percentage of a basal value, i.e. the value determined for cells that have not been brought into contact with any compound to be screened, such as the value determined for cells brought into contact with a "blank sample" (liquid phase only).

It should be realized that the identification of the candidate compound based on the determined mTORC2 activity and Akt activity is not limited to any of the above calculations, which are provided as examples only.

For example, the candidate compound may be identified without calculating any particular ratio, e.g. by simple visual inspection of results, such as for example a western blot.

The screening method may be performed using one target cell type, representative for one or more particular tissues of a mammalian body. The screening method however may be expanded to a panel comprising any number of different cells, thereby allowing for the verification of a selectivity of the compound for a target cell type and/or the absence of stimulation of Akt activity in the target cell type as well as in other mammalian cell types.

Thus, in some embodiments, the screening method of the invention is performed using more than one cell type representative for one or more different tissues of a mammalian body. For example, a screening method of the invention may involve the use of a panel of cells selected from e.g. muscle cells, adipocytes, such as brown fat cells and white fat cells, beta cells, brain cells, liver cells, reproductive cells and cells involved in reproduction, and mammary cells.

In some embodiments, when the screening method is performed on a panel of different cells, at least some cells are muscle cells, and at least some other cells are not muscle cells.

Thus, in some embodiments, the screening method of the invention comprises:
providing different cells expressing mTOR, at least some of which also express Akt;
bringing a compound into contact with the cells;
determining the mTORC2 activity in the cells, and
identifying a candidate compound based on a difference in mTORC2 activity determined in the different cells and based on the determined Akt activity.

In some embodiments, the screening method of the invention comprises:
providing a first and a second cell, both expressing mTOR and being capable of activating mTORC2 and wherein at least the first cell expresses Akt and is capable of activating Akt;
bringing a compound into contact with the first and the second cell;
determining a change in mTORC2 activity in the first and in the second cell, and
identifying a compound that causes a higher increase of mTORC2 activity in the first cell than in the second cell.

In some embodiments, both the first and the second cell express Akt and both the first and the second cell is capable of activating Akt.

Preferably, the method also comprises determining the effect of the contacting on the activity of Akt in at least the first cell. In some embodiments, the method comprises determining the effect of the contacting on the activity of Akt in both the second and the first cell.

In some embodiments, the first cell is a muscle cell, e.g. a skeletal muscle cell, and the second cell is mammalian non-muscle cell, e.g. an adipocyte, such as a white fat cells.

In some embodiments of the screening method of the invention, at least the first cell comprises a GPCR. In some embodiments, both cells comprise a GPCR.

In some embodiments of the screening method of the invention, at least the first cell comprises a GLUT. In some embodiments, both cells comprise a GLUT.

For example, in one embodiment, the screening method is a method for identifying a candidate compound for use in the treatment of a condition involving a dysregulation of glucose homeostasis or glucose uptake in a tissue having cells that contain GLUT4 as a glucose transporter, in particular muscles, such as skeletal muscles, but also cardiac muscle.

In another embodiment, the screening method is a method for identifying a candidate compound for use in the treatment of a condition involving a dysregulation of glucose homeostasis or glucose uptake in a tissue having cells that contain GLUT1 as a glucose transporter, such as the epithelial cells of the blood-brain barrier.

A candidate compound identified by the screening method of the invention might work on all tissues of the body, or display tissue specificity. The effect(s) of either known or unknown drugs on translocation of any GLUT, e.g. GLUT4, can be further assessed in vivo, e.g. by constructing a mouse that expresses GPCR and/or GLUT containing a tag preferable a fluorescent protein. After administration of the compounds to the test animal, all tissues can be evaluated for GPCR activation and GLUT translocation.

By the screening method of the present invention, compounds may be identified for the treatment of any condition involving a dysregulation metabolism in a mammal, in particular a condition involving a dysregulation of glucose homeostasis or glucose uptake in the mammal. In one aspect, thus a compound is provided, for use in the treatment of a condition involving a dysregulation of glucose homeostasis or glucose uptake in a mammal, which is a compound that does not cause a significant increase of the Akt production in the cells of the mammal, but that causes an increase of the GLUT translocation in at least some cells of the mammal, in particular in muscle cells, such as skeletal muscle cells.

In one aspect a kit is provided, for use in a method of screening for a candidate compound for the treatment of a condition involving a dysregulation of metabolism in a mammal, e.g. a dysregulation of glucose homeostasis or glucose uptake, said kit comprising cells capable of expressing mTOR and Akt, together with instructions for use of the kit.

In some embodiments, the kit comprises a cell capable of expressing a GPCR and of expressing mTOR.

In some embodiments, the kit comprises a cell capable of expressing a GPCR and of expressing a GLUT.

In some embodiments, the kit comprises a compound that is a known Act agonist, for use as a reference in the determination of Akt activity.

In some embodiments, the kit comprises a compound that is a known mTORC2 agonist, such as isoproterenol, for use as a reference in the determination of mTORC2 activity.

In some embodiments, the kit comprises a GPCR agonist, such as noradrenaline.

A cell for use in a kit of the invention e.g. is derived from primary cultures from heart, skeletal muscle, brown fat, white fat, brite/beige fat, liver, brain, mammal gland and other mammalian tissues. The cell or cells to be used in the kit generally is selected so as to be representative of the tissue(s) involved or afflicted by the condition, disease or disorder. For example, if the kit is for use in a screening method directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the kit is for use in a screening method directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be used in the kit of the present invention include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with introduced mTOR and/or Akt and/or GPCR and/or GLUT can also be included in the kit of the invention, e.g. a cell that is transfected and expresses (or overexpresses) any of said proteins, for example a CHO cell line.

Another aspect relates to methods for treatment of a condition involving a dysregulation of metabolism of a mammal, in particular a dysregulation of glucose homeostasis or glucose uptake, e.g. any of the conditions mentioned herein above. In particular, this aspect is directed to a method of preventing, curing or inducing durable long term remissions in a mammal suffering from any such condition, or a mammal that is susceptible to develop any such condition, as well as any other mammalian condition in which glucose homeostasis and glucose uptake into cells contribute to the condition. The invention is in particular concerned with GPCRs ability to increase glucose uptake without stimulating Akt as a mechanism for treating a mammalian disease.

One further aspect relates to methods of restoring or enhancing glucose uptake in tissues by translocation of GLUT, said translocation being achieved by stimulating GPCRs in such a way that said receptors do not stimulate Akt.

According to the present invention, such stimulation (or modulation) may be achieved pharmacologically with compounds (both small and large molecules), that either bind a GPCR directly or stabilize the GPCR in such a way that glucose uptake is enhanced without an increase of Akt. The modulation can also be achieved by stimulating mTORC2 directly or indirectly to activate glucose uptake without stimulating Akt.

Depending on the cellular context, any of the mentioned activities will lead to alteration and/or increase in the GPCR signaling cascade coupled to glucose uptake, resulting in improvements relevant to the disease states of interest as will be discussed in detail herein below.

The method of the invention involves the stimulation (i.e. enhancement or increase) of GLUT translocation, preferably GLUT1 or GLUT4 translocation. Translocation of GLUT promotes glucose uptake and alters cell and tissue functions particular to the specific target tissues including heart muscle, skeletal muscle and others tissues expressing various glucose transporters. Methods that promote specific GLUT translocation by stimulating specific receptors in specific tissues can target or prevent specific diseases involving those specific tissues or cells. For example, stimulation of GLUT4 translocation in white adipocytes and skeletal muscle will improve glucose homeostasis. Drugs that stimulate GLUT4 translocation will thus improve, prevent, or cure different conditions involving a dysregulation of glucose homeostasis or glucose uptake in a mammal, in particular type 2 diabetes. Further, the functional activity of GLUT4 translocation can be modulated in human beings and other mammals in order to ameliorate or even prevent diabetes and reduce the need for other medicaments.

Thus, in one embodiment of the invention, there is provided a method of treatment of a mammal subject, preferably a human, suffering from or susceptible to develop a disease that is induced by, regulated by, or associated with, changes in glucose homeostasis, by a compound that upregulates translocation of GLUT, e.g. GLUT4, in peripheral tissues of said subject.

As noted herein above, GLUT4 is mainly expressed in heart, skeletal muscle and fat (white fat, brown fat and brite/beige), but GLUT4 has also been reported to be expressed in brain, kidney, liver and other tissues. Regulation of GLUT4 translocation in either of these tissues will affect the function of these. An enhanced translocation of GLUT4 will help keeping glucose levels in the blood under control and prevent diabetes and related disorders that are modulated by GLUT4 translocation and glucose uptake. In another aspect an increase of GLUT1 translocation in brown fat will lead to increased glucose uptake from the blood to prevent diabetes and related disorders.

In another aspect an increase of GLUT1 and/or GLUT3 translocation in brain will lead to increased glucose uptake from the blood into brain, which may be useful in the treatment of degenerative diseases of the central nervous system such as Alzheimer's disease. Therefore, in one embodiment of the invention, a method for the treatment of a degenerative disease of the central nervous system, such as Alzheimer's disease, is provided, by administration of a GPCR ligand capable of stimulating translocation of GLUT, e.g. of GLUT selected from GLUT1 and GLUT3.

In another aspect an increase of GLUT1 and/or other GLUT translocation in brown adipose tissue or brite/beige adipose tissues will lead to increased glucose uptake from the blood into the tissue, which may be useful in treatment of a condition involving a dysregulation of glucose metabolism in a mammal, such diabetes. Therefore, in one embodiment of the invention, a method for the treatment of diabetes by administration of a GPCR ligand capable of stimulating translocation of GLUT, e.g. of GLUT is selected from the family of GLUTs.

Impaired GLUT translocation also plays a role in muscle wasting and stimulation of GLUT translocation will reduce muscle wasting.

GLUT translocation also plays a role in feeding behavior. Mice lacking GLUT4 develop problems with lipid and glucose homeostasis leading to changes in feeding behavior. Therefore, in some embodiments of the invention, a method of treating muscle wasting or a disordered feeding behavior is provided, or a method of treating disrupted lipid or glucose homeostasis, by administration of a GPCR ligand capable of stimulating translocation of GLUT, e.g. of GLUT4.

Further, GLUT, e.g. GLUT8, has been reported as involved in both male and female infertility. Therefore, in some embodiments of the invention, a method of treating male or female infertility is provided, by administration of a beta-adrenergic ligand capable of stimulating translocation of GLUT, e.g. of GLUT8.

In another aspect, a compound is provided, suitable for use in the treatment of a condition involving a dysregulation of glucose homeostasis or glucose uptake in a mammal which is a compound that does not cause an increase of the Akt activity in the cells of the mammal, that causes an increase of the GLUT translocation in at least some cells of the mammal, in particular in muscle cells, such as skeletal muscle cells, and that does not cause an increase of the GLUT translocation in other cells of the mammal, in particular adipocytes, such as white fat cells.

One aspect of the present invention relates to a method of treatment of a condition involving a dysregulation of glucose homeostasis or glucose uptake in a mammal, comprising the administration of a therapeutic effective amount of one or more compounds that bind GPCR, said binding causing an increase of mTORC2 activity and GLUT translocation in cells of the mammal, in particular muscle cells of the mammal, without causing any substantial increase of the Akt production in the cells of the mammal, to a mammal in need of such treatment.

Another aspect of the present invention relates to the use of a compound identified in a screening method of the present invention, in the manufacturing of a medicament for use in the treatment of a condition involving a dysregulation of glucose homeostasis or glucose uptake in a mammal.

Still another aspect relates to a pharmaceutical composition comprising a compound identified in a screening method of the present invention. Still another aspect relates to a compound identified in a screening method of the present invention.

Therapeutically effective means an amount of compound which is effective in producing GLUT translocation. Administration means delivering the compound of the present invention to a mammal by any method for example, orally, intravenously, intramuscularly, topically, transdermal, or inhalation.

Carriers for the administration include any carrier known in the art including water, saline, phosphate buffered saline, dextrose, glycerol, ethanol and similar carriers and combination of these. Carriers can also comprise wetting or emulsifiers, preservatives or buffers that enhance effectiveness, half-life, and shelf life of the compound(s).

Furthermore additional carriers influencing the release of the compound(s) including how quick, sustained or delayed the active compound(s) is released when administered to the mammal.

The composition of this invention can be any form including solid, semi-solid and liquid such as used in tablets, pills, powders, solutions, dispersions, suspensions, liposomes suppositories, injections and infusible solutions.

The methods and compositions of the invention can be administered to any suitable mammal such as rabbit, rat or mouse or more preferable a human.

While this invention has been described with respect to various specific examples it is to be understood that the invention is not limited by this and it can be variously practiced within the scope of the claims. The invention is further illustrated by the following non-limiting examples.

EXAMPLES

Example 1

Glucose uptake was measured in CHO Glut 4 (Chinese Hamster Ovary cells transfected to overexpress GLUT4) and L6-myotubes grown in 12-well plates using $^3$H-2-dexoyglucose as previously described (Nevzorova et al. 2006, Dehvari et al. 2011, Nevzorova et al. 2002) with minor modifications. L6-cells were differentiated for 7-8 days before the experiment, serum-starved over night in media containing 0.5% fatty-acid free BSA and stimulated with test compounds for totally 2 h, unless otherwise stated. The test compounds used in the experiment were: N-[5-(4,5-dihydro-1H-imidazol-2yl)-2-hydroxy-5,6,7,8-tetrahydro naphthalen-1-yl]methanesulfonamide hydrobromide (A61603), noradrenaline (NA), insulin, oxymetazoline (oxy), and 5-(methylamino)-2-({(2R,3R,6S,8S,9R,11R)-3,9,11-trimethyl-8-[(1S)-1-methyl-2-oxo-2-(1H-pyrrol-2-yl)ethyl]-1,7-dioxaspiro[5.5]undec-2-yl}methyl)-1,3-benzoxazole-4-carboxylic acid (also referred to as Calcimycin) (A23187).

Inhibitors were added 30 min before stimulation. 25 min before the end of the experiment, cells were washed twice in warm PBS and kept in glucose-free DMEM together with the different drugs for 10 min before 50 nM $^3$H-2-dexoyglucose was added for additional 6 minutes. The reaction was terminated by washing the cells in ice-cold PBS three times. Cells were lysed in 0.2 NaOH for 1 h in 60° C. and the radioactivity detected by liquid scintillation (scintillation buffer Emulsifier Safe, Perking Elmer and analysis is a Tri-Carb® 2800TR from Perkin Elmer).

As shown in FIG. 1, stimulation with the classical adrenergic agonists such as noradrenaline (NA) increases glucose uptake in CHO glut 4.

Figure 2:
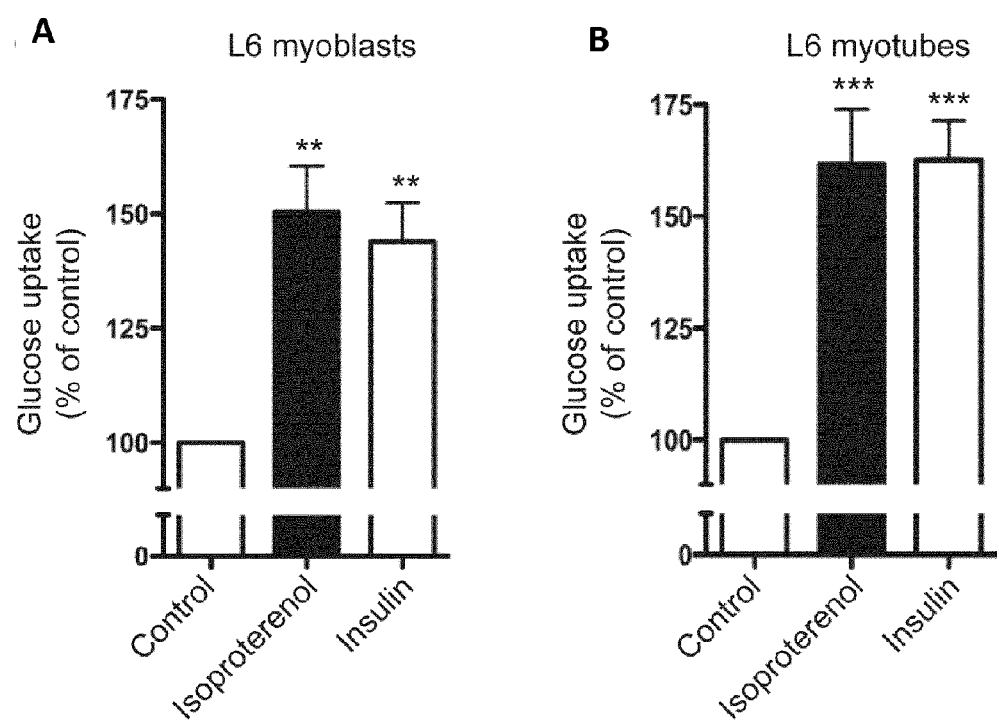
FIG. 2 is a bar chart showing glucose uptake (% of control) in (A) L6 myoblasts brought into contact with isoproterenol and insulin, respectively; and in (B) L6 myotubes brought into contact with isoproterenol and insulin, respectively.

Furthermore, under similar conditions, glucose uptake is increased in both L6 myoblasts and L6 myotubes (FIG. 2) treated with isoproterenol or insulin. This illustrates that GPCR agonists, such as isoproterenol, can stimulate glucose uptake in both undifferentiated and differentiated peripheral cell types such as skeletal muscle.

Next, L6 cells were grown in 4- or 8-well culture chamber slides (BD Biosciences, Franklin Lakes, BJ), treated with isoproterenol or insulin (or untreated for control), washed in DMEM and fixed with 4% formaldehyde in PBS, quenched with 50 mM glycine in PBS for 10 min, and blocked with 5% BSA in PBS. PIP3 was visualized in permeabilised L6 cells (0.5% Triton X-100 in water, 15 min) blocked with 10% rat serum in TBS overnight at 4° C. Mouse anti-PIP3 conjugated to a biotinylated goat anti-mouse IgM diluted 1:100 was incubated for 1 h at 37° C., cells washed three times (10% rat serum in TBS), secondary antibody added (streptavidin-Alexa Fluor® 488 1:2000 in TBS, 30 min, 37° C.). Slides were mounted with ProLong® Gold antifade reagent (Invitrogen). Images were observed in an inverted laser-scanning microscope (LSM 510META; Carl Zeiss, Advanced Imaging Microscopy, Jena, Germany).

Figure 3:
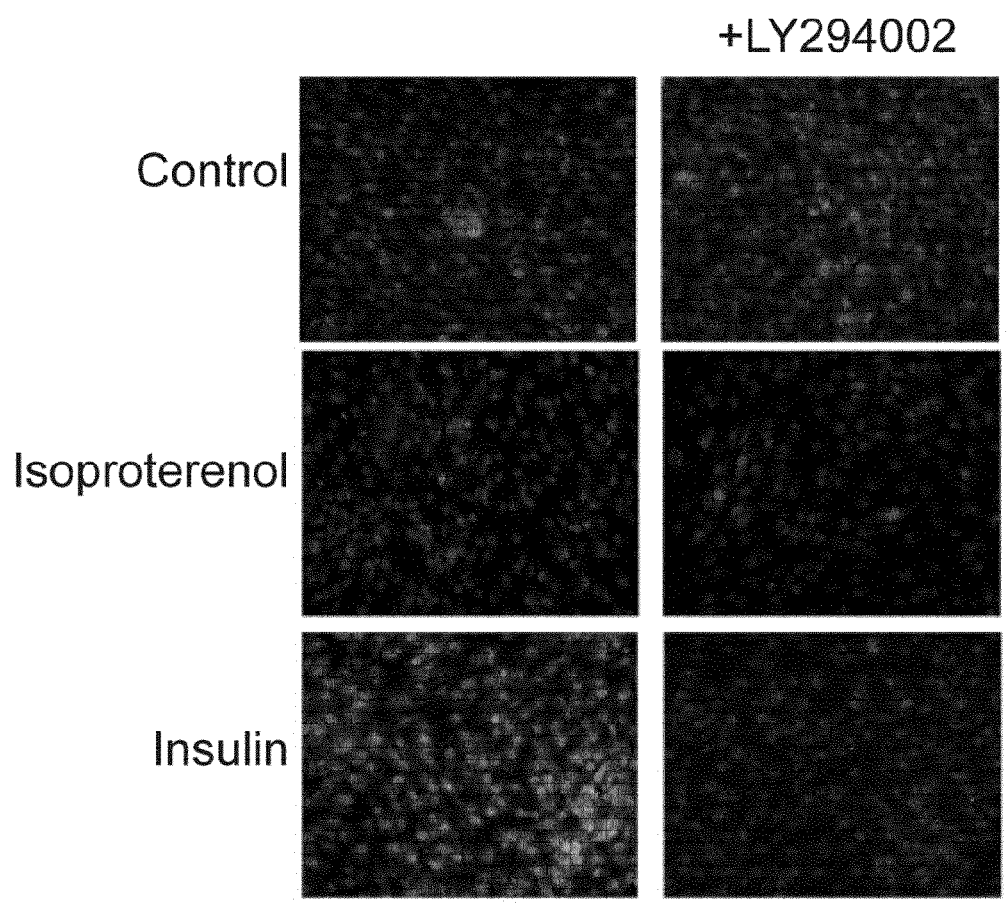
FIG. 3 shows fluorescence in L6 cells treated with insulin or isoproterenol, or untreated for control. The presence of PIP3 in permeabilized L6 cells was observed in an inverted laser-scanning microscope, using mouse anti-PIP3 conjugated to a biotinylated goat anti-mouse IgM and streptavidin-Alexa Fluor® 488 as secondary antibody.

Insulin but not isoproterenol increased PIP3 content and this was inhibited by LY294002 (FIG. 3), which is an inhibitor of phosphoinositide 3-kinases (PI3Ks). This illustrates that PI3 kinase and PIP3 stimulation is not involved in GPCR stimulated glucose uptake.

Figure 4:
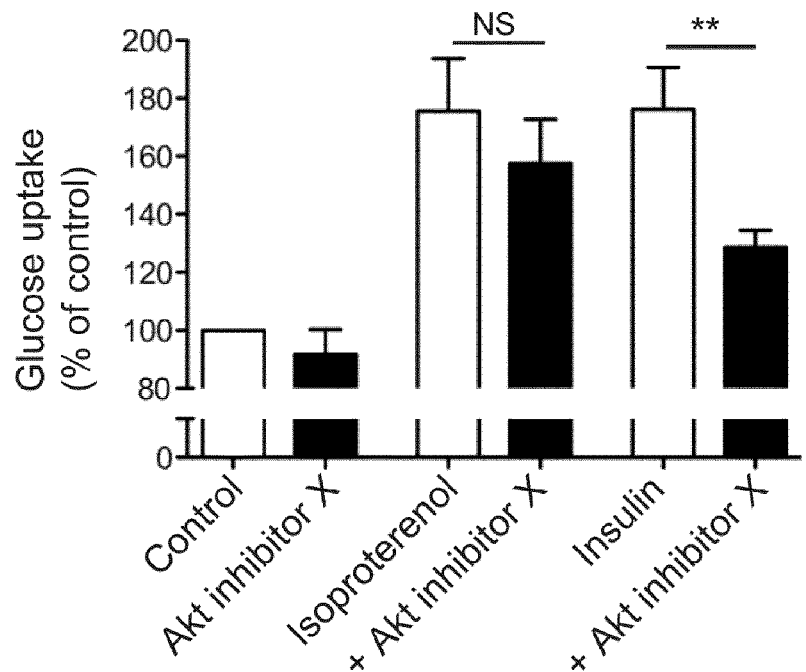
FIG. 4 is a bar chart showing glucose uptake (% of control) in L6 myotubes in the presence of insulin and isoproterenol, respectively, and in the presence or absence of Akt inhibitor X.

The glucose uptake in L6 myotubes was also studied under similar conditions in the presence of the Akt inhibitor X (10 µM), that prevents Akt activation by interfering with the phosphatidyl-binding domain of Akt. As shown in FIG. 4, inhibitor X inhibited insulin-stimulated glucose uptake but not GPCR-mediated glucose uptake. This indicates that Akt is not involved in GPCR stimulated glucose uptake.

L6 myotubes (FIG. 5) and CHO GLUT4 cells (FIG. 6) in 12-well plates were used for western blotting. Cells were serum-starved overnight before experiment. Immunoblotting was performed as previously described (Nevzorova et al. 2006, Dehvari et al. 2011, Nevzorova et al. 2002). Primary antibodies (Akt, phospho-Akt T308, phospho-Akt S473, AS 160, GLUT4, phospho-mTOR S2448, phospho-mTOR S2481, raptor, and rictor diluted 1:1000) were all from Cell Signaling Technology, Inc and were detected using a secondary antibody (horseradish peroxidase-linked anti-rabbit IgG, from Cell Signaling Technology, Inc) diluted 1:2000 and measured using enhanced chemiluminescence (ECL, Amersham Biosciences).

Figure 5:
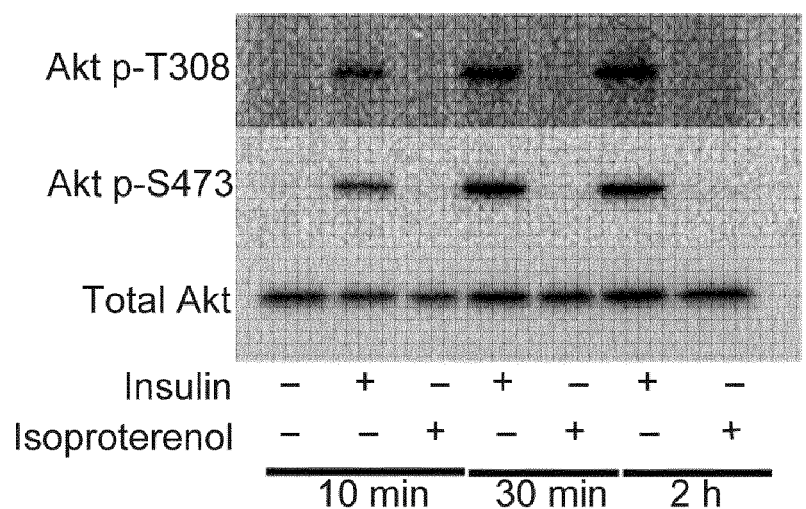
FIG. 5 is a western blot showing total Akt, Akt phosphorylated on T308 (Akt p-T308) and Akt phosphorylated on S473 (Akt p-T473), respectively, in L6 myotubes, after contact (+) of the cells with insulin or isoproterenol for 10 minutes, 30 minutes and 2 hours, or, for control cells, after 10 minutes in the absence (−) of insulin and isoproterenol.
Figure 6:
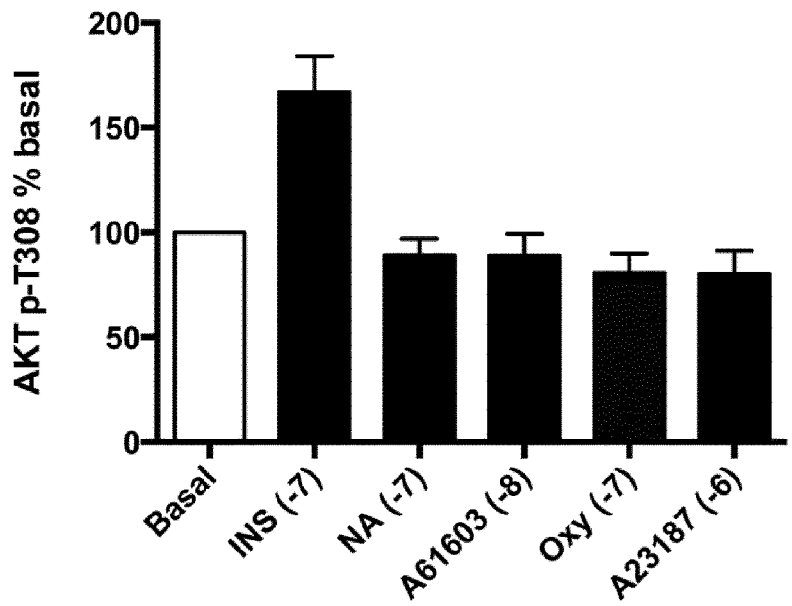
FIG. 6 is a bar chart showing Akt phosphorylated on (A) T308 or (B) S473 in % of basal Akt phosphorylation, in CHO GLUT4 brought into contact for 10 min with insulin (INS (0.1 µM)), noradrenaline (NA (0.1 µM)), A61603 (0.01 µM), oxymetazoline (oxy (0.1 µM)), and A23187 (0.1 µM), respectively. Numbers in brackets in figure represent log concentration.
Figure 6:
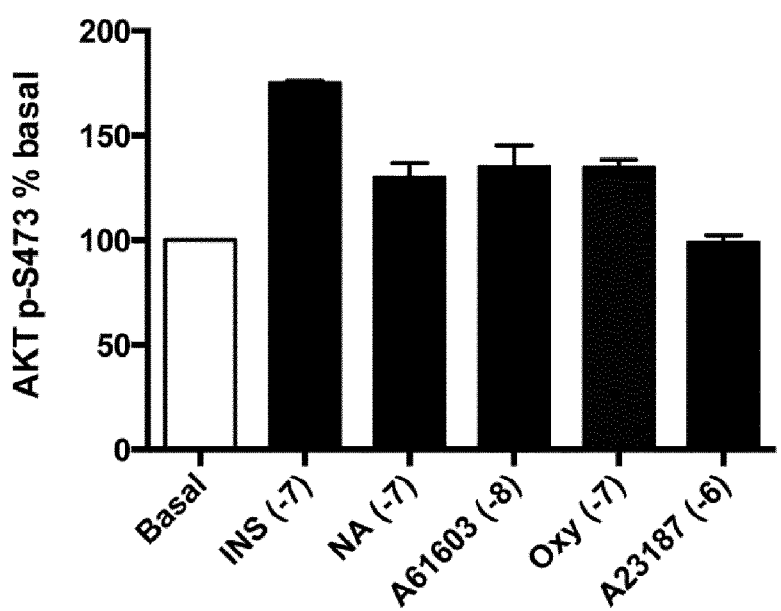
Figure 7:
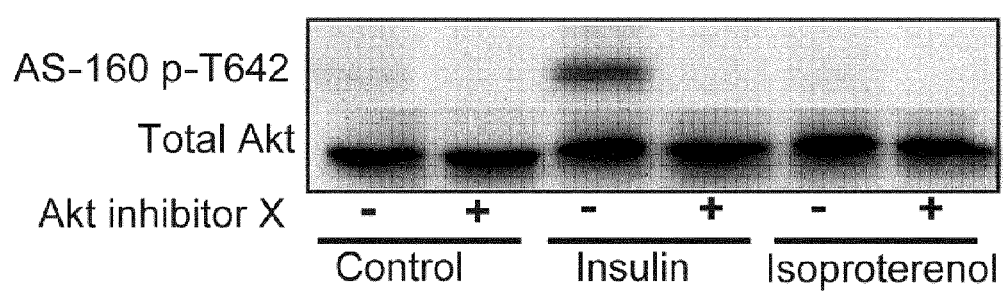
FIG. 7 is a western blot showing total Akt and Akt downstream target AS160 phosphorylated on T642 (AS-160 p-T642), respectively, in L6 myotubes, after contact of the cells with insulin or isoproterenol in the presence (+) or absence (−) of Akt inhibitor X or, for control cells, in the absence of insulin and isoproterenol and in the presence (+) or absence (−) of Akt inhibitor X.

Akt is downstream of PI3K, but clearly not phosphorylated at T308 or S473 following GPCR stimulation, whereas insulin increased Akt phosphorylation at both sites at all time points examined (FIG. 5, FIG. 6). This illustrates that Akt is not involved in GPCR stimulated glucose uptake AS160 was also phosphorylated following insulin but not isoproterenol treatment, in an Akt-dependent manner (FIG. 7). These results emphasize that GPCR-stimulated glucose uptake does not utilize major components of the insulin pathway.

Example 2

Figure 8:
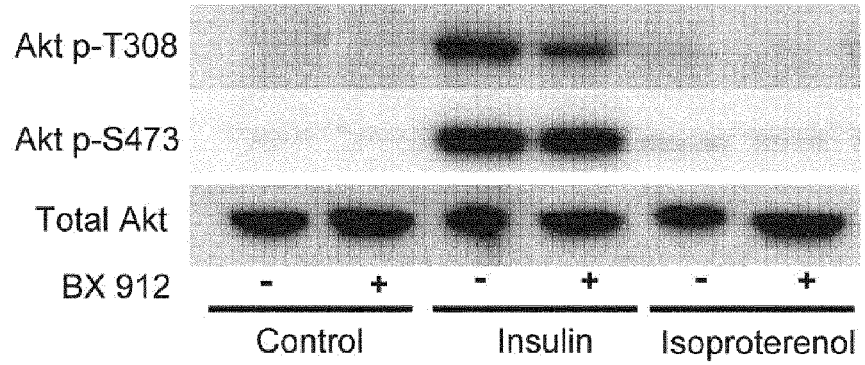
FIG. 8 is (A) a western blot showing total Akt, Akt phosphorylated on T308 and Akt phosphorylated on S473, respectively, in L6 myotubes, after contact of the cells with insulin or isoproterenol in the presence (+) or absence (−) of the PDK1 inhibitor BX-912 or, for control cells, in the absence of insulin and isoproterenol and in the presence (+) or absence (−) of the PDK1 inhibitor BX-912; (B) a bar chart showing the ratio of Akt phosphorylated on T308 to total Akt, as a percentage of the same ratio in control cells, in the cells treated with insulin or isoproterenol in the absence (−BX 912) or presence (+BX 912) of BX-912; and (C) a bar chart showing the ratio of Akt phosphorylated on S473 to total Akt, as a percentage of the same ratio in control cells, in the cells treated with insulin or isoproterenol in the absence (−BX 912) or presence (+BX 912) of BX-912.
Figure 8:
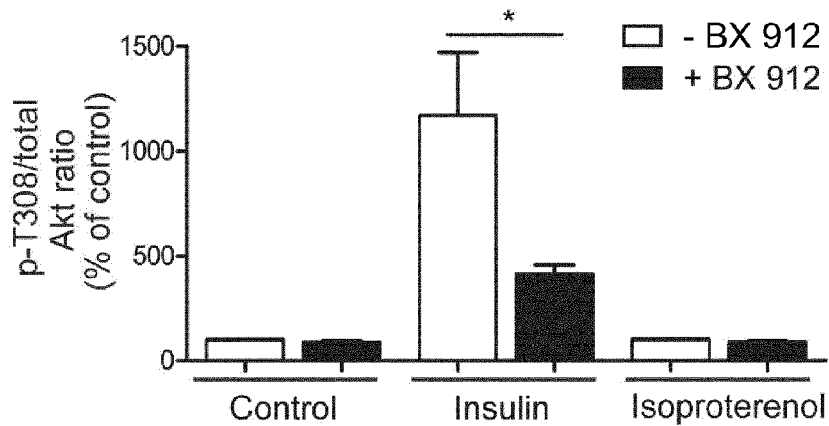
Figure 8:
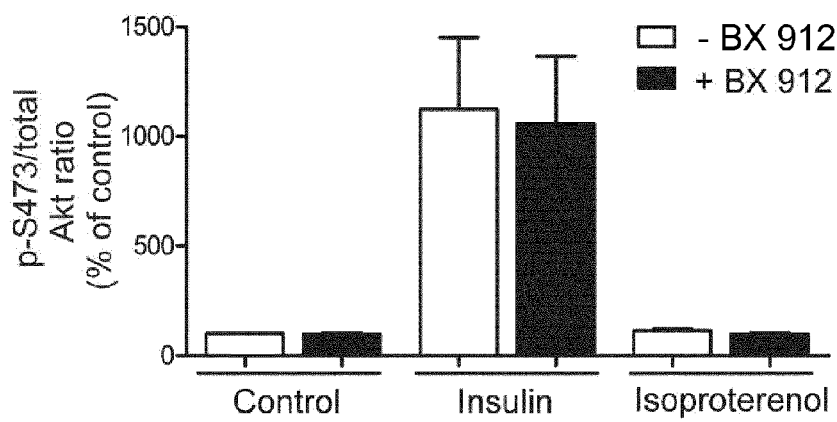

The PDK1 inhibitor BX-912 significantly inhibited insulin-mediated T308-Akt phosphorylation but had no effect on S473-Akt phosphorylation, which indicates that PDK1 is upstream of Akt in the insulin pathway (FIG. 8). Thus the GPCR pathway to increased glucose uptake does not utilize PI3Ks or converge with the insulin pathway at the level of Akt.

Figure 9:
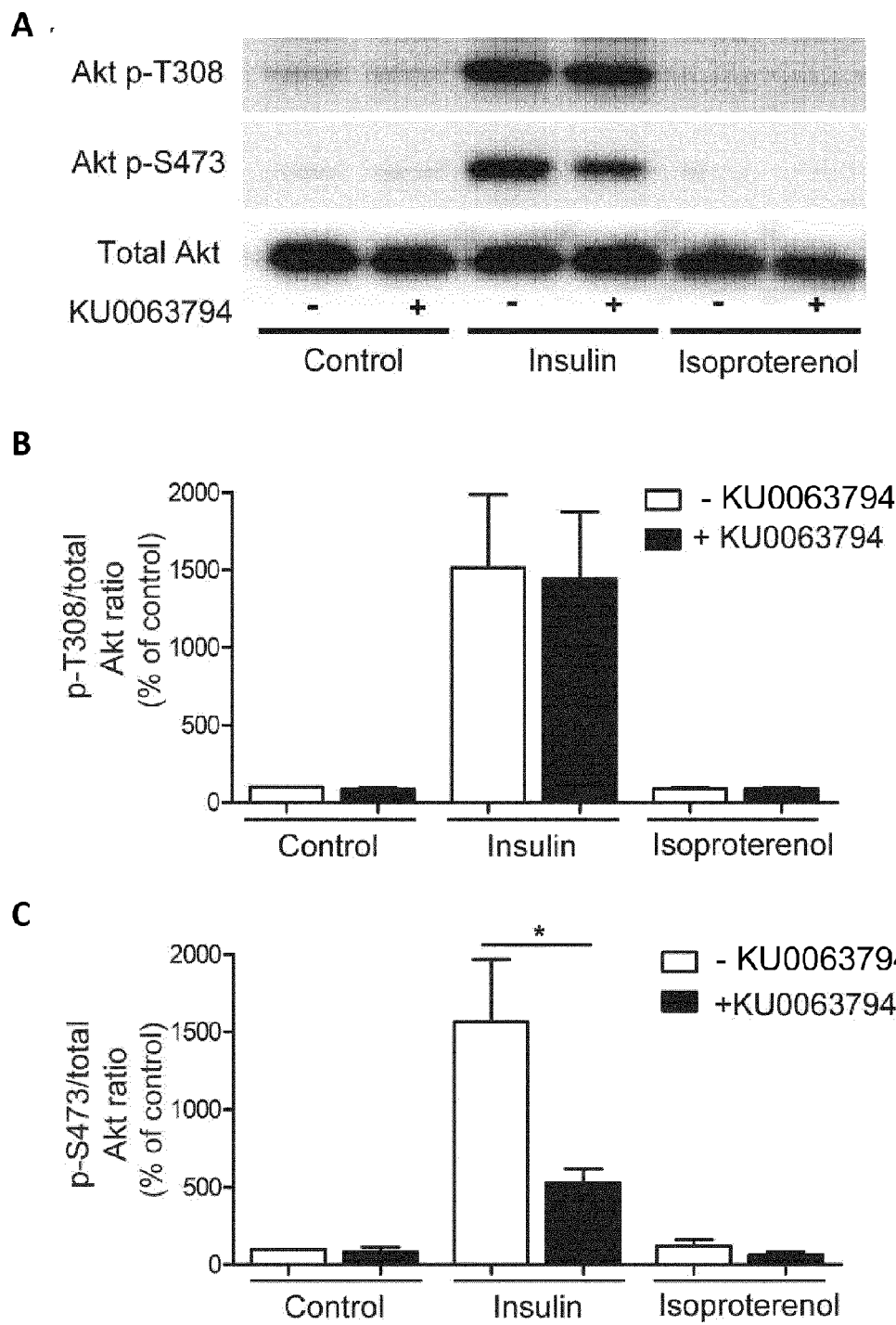
FIG. 9 is (A) a western blot showing total Akt, Akt phosphorylated on T308 and Akt phosphorylated on S473, respectively, in L6 myotubes, after contact of the cells with insulin or isoproterenol in the presence (+) or absence (−) of the mTOR inhibitor KU0063794 or, for control cells, in the absence of insulin and isoproterenol and in the presence (+) or absence (−) of the mTOR inhibitor KU0063794; (B) a bar chart showing the ratio of Akt phosphorylated on T308 to total Akt, as a percentage of the same ratio in control cells, in the cells treated with insulin or isoproterenol in the absence (−KU0063794) or presence (+KU0063794) of KU0063794; and (C) a bar chart showing the ratio of Akt phosphorylated on S473 to total Akt, as a percentage of the same ratio in control cells, in the cells treated with insulin or isoproterenol in the absence (−KU0063794) or presence (+KU0063794) of KU0063794.

Following insulin receptor activation, Akt is phosphorylated on S473 by mTOR (Hawkins et al. 2006) that exists as two complexes, mTOR complex-1 (mTORC1) and mTOR complex-2 (mTORC2). KU0063794 (KU) is a potent mTOR inhibitor with an $IC_{50}$ of 10 nM that does not inhibit other members of the PI3K/PIKK family at up to 1 µM (Garcia-Martinez et al. 2009). KU (100 nM) had no effect on insulin-stimulated phosphorylation of Akt at T308 but decreased Akt phosphorylation at S473 (FIG. 9). GPCR stimulation did not stimulate Akt phosphorylation. This illustrates that Akt phosphorylation can be used as a marker for differentiation between compounds that activate glucose uptake through Akt or not.

Example 3

Figure 10:
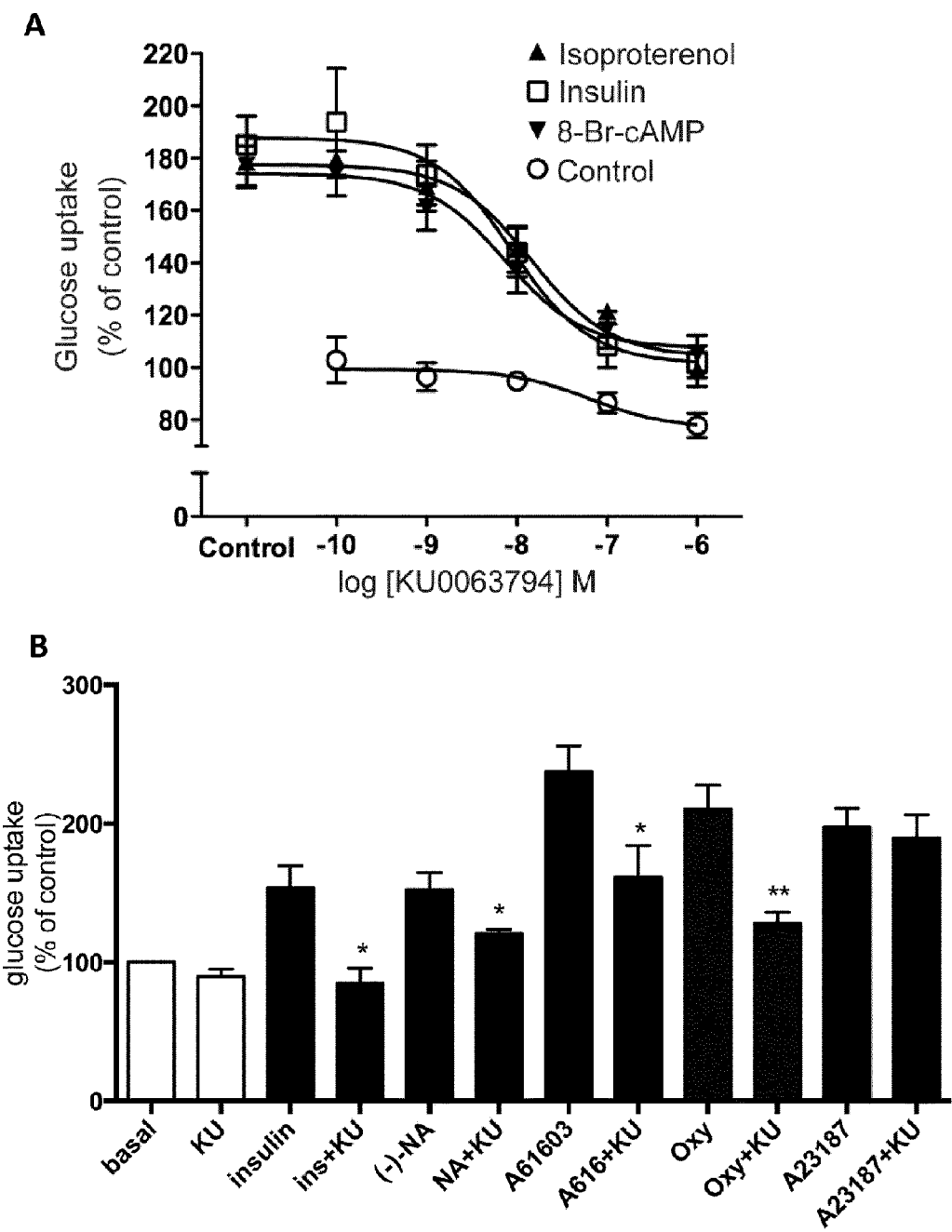
FIG. 10 is (A) a semi-logarithmic graph showing glucose uptake (% of control) in L6 myotubes in the absence (control) or presence of isoproterenol (0.1 µM), insulin (0.1 µM) or 8-Br-cAMP (10 µM), and in the presence of different concentrations of the mTOR inhibitor KU0063794; and (B) a bar chart showing glucose uptake (% of control) in CHO GLUT4 cells brought into contact with insulin, noradrenaline (NA), A61603, oxymetazoline (oxy), and A23187, (concentrations as in FIG. 6) in the absence or presence of KU0063794 (+KU).

The mTOR inhibitor KU inhibits GPCR stimulated glucose-uptake in L6 myotubes (A) and CHO glut 4 (B) (FIG. 10) indicating that GPCR stimulate glucose uptake through mTOR but as exemplified above not through Akt activation.

Soleus muscles were dissected from Sprague-Dawley rats and suspended in Krebs-Henseleit bicarbonate (KHB) buffer (118.5 mM NaCl, 4.7 mM KCl, 1.2 mM $KH_2PO_4$, 25 mM $NaHCO_3$, 2.5 mM $CaCl_2$, 1.2 mM $MgSO_4$, 5 mM HEPES) in organ baths containing 30 ml KHB containing 5 mM glucose and 15 mM mannitol, bubbled with 95% $O_2$/5% $CO_2$ (pH 7.4) and maintained at 37° C. Incubation with KU0063794 or vehicle was for 30 min followed by insulin or isoproterenol for 1 h. Muscles were rinsed with KHB (20 mM mannitol) for 10 min, then incubated in KHB (8 mM 3-O-methylglucose and 12 mM mannitol with 438 µCi/mmol 3-O-methyl[$^3$H]glucose (80.2 Ci/mmol; PerkinElmer) and 42 µCi/mmol [$^{14}$C] mannitol (58.8 mCi/mmol; PerkinElmer, USA)) for 12 min Muscles were then rinsed with PBS and frozen in liquid nitrogen, weighed and dissolved in 1 mL of 0.5M NaOH at 60° C. $^3$H and $^{14}$C were measured by liquid scintillation counting. Total muscle 3-O-methylglucose and extracellular space were measured as described previously (23). Intracellular 3-O-methylglucose accumulation was calculated by: (Total muscle 3-O-methylglucose)–(extracellular 3-O-methylglucose)=intracellular 3-O-methylglucose. This is then expressed as a rate of 3-O-methylglucose transport per mL of intracellular water per hour.

Groups of wild-type (WT) 129sv mice were fasted for 5 h and anesthetized with 60 mg/kg pentobarbital i.p. Mice were injected with KU0063794 (10 mg/kg) or DMSO 10 min before insulin (1 mg/kg), isoproterenol (1 mg/kg) or saline. After 20 min [$^3$H]-2DG (130 µCi/kg) was injected. Muscles were sampled 1 h later and lysed in 0.5M NaOH. Glucose uptake was measured by liquid scintillation counting.

Figure 11:
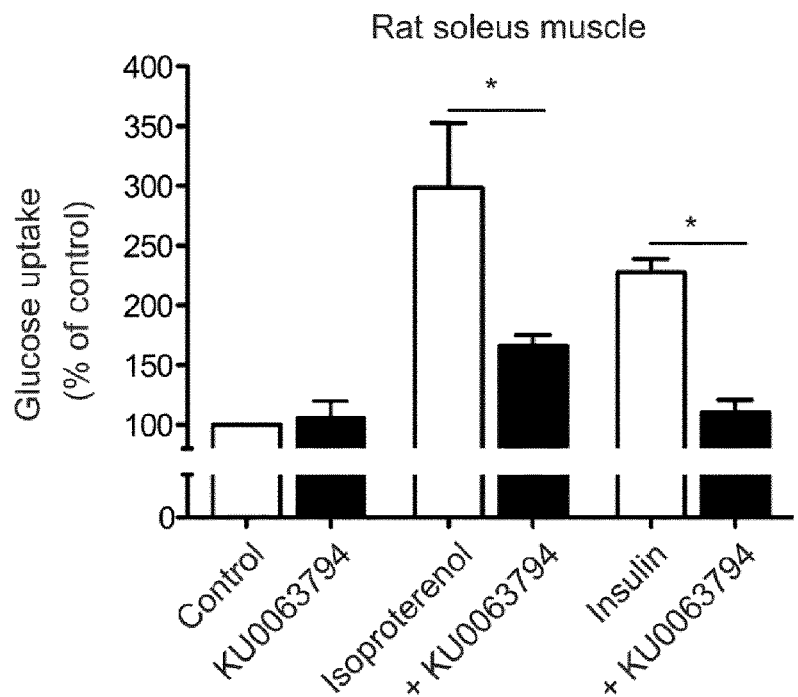
FIG. 11 is a bar chart showing glucose uptake (% of control) in rat soleus muscle in the absence (control) or presence of insulin or isoproterenol, respectively, and in the in the absence or presence (+KU0063794) of KU0063794.
Figure 12:
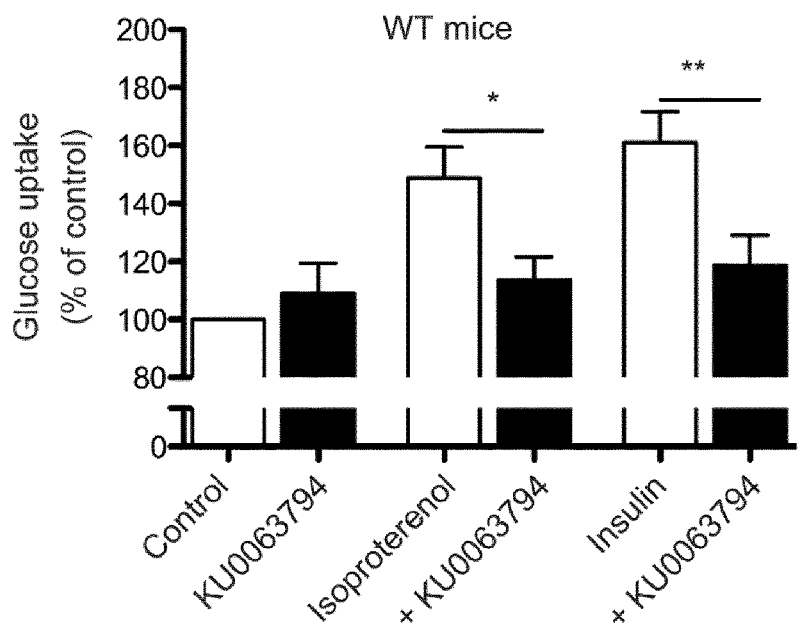
FIG. 12 is a bar chart showing glucose uptake (% of control) in WT mice in the absence (control) or presence of insulin or isoproterenol, respectively, in the absence or presence (+KU0063794) of KU0063794.

In intact rat soleus muscle (FIG. 11) and in vivo using mouse skeletal muscles, (FIG. 12), mTOR had a key role in GPCR stimulated glucose uptake. This indicates that GPCRs stimulate glucose uptake in peripheral tissues in animals via mTOR.

Figure 13:
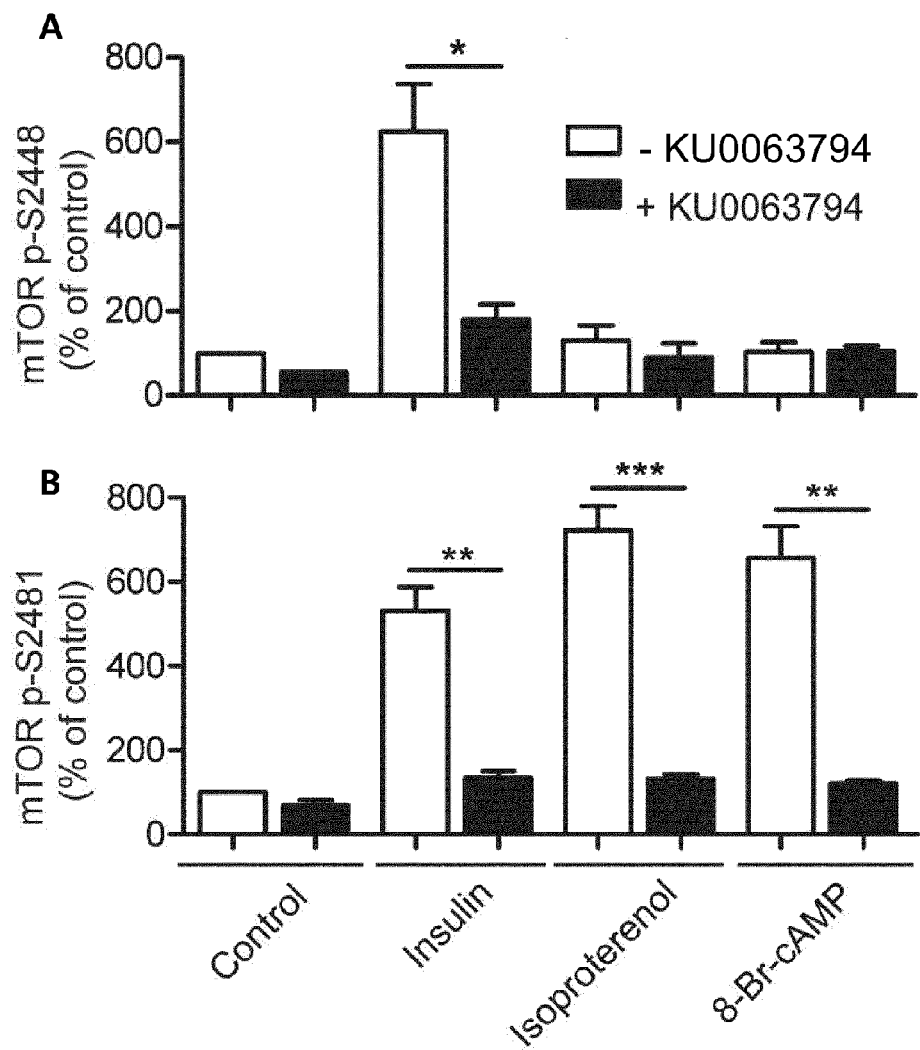
FIG. 13 is (A) a bar chart showing phosphorylation (% of control) of mTOR on S2448 (mTOR p-S2448) in L6 myotubes (control) and in L6 myotubes treated with (from left to right:) insulin, isoproterenol or 8-Br-cAMP, respectively, in the absence (−KU0063794) or presence (+KU0063794) of KU0063794, and (B) a bar chart showing phosphorylation (% of control) of mTOR on S2448 (mTOR p-S22481) in L6 myotubes (control) and in L6 myotubes treated with insulin, isoproterenol or 8-Br-cAMP, respectively, in the absence (−KU0063794) or presence (+KU0063794) of KU0063794.

The protein mTOR can be phosphorylated at two sites, S2448 that predominates in mTORC1 and S2481 that is more associated with mTORC2 (Copp, Manning & Hunter 2009). Insulin stimulation caused phosphorylation of mTOR at both S2448 and S2481 whereas treatment with the GPCR agonist isoproterenol induced phosphorylation only at S2481 (FIG. 13). Although the insulin and GPCR pathways converge at mTOR, the activation mechanisms are different: One particular difference is that GPCR signaling does not involve Akt whereas in the insulin signaling pathway, Akt is downstream of mTORC2, which phosphorylates Akt on S473 (Hresko, Mueckler 2005). Subsequently this leads to phosphorylation of S2448 on mTORC1 (Nave et al. 1999, Sekulic et al. 2000). Insulin thus activates both mTORC1 and mTORC2 while GPCR stimulation only activates mTORC2.

In short, insulin treatment caused robust phosphorylation of mTOR at both S2448 and S2481, whereas GPCR stimulation phosphorylated mTOR only at S2481. Phosphorylation at these sites was abolished for both insulin and GPCR stimulation by the mTOR inhibitor KU. In skeletal muscle, while both insulin and isoproterenol cause mTOR phosphorylation at S2481, only insulin causes phosphorylation of Akt at S473. It is known that mTORC2 is associated with lipid rafts and that Akt when activated by tyrosine kinases also migrates to these structures where the proteins can interact. The fact that GPCR stimulation does not lead to Akt activation suggests that the interaction with mTORC2 is not possible, which explains the lack of phosphorylation of S473.

mTOR is involved in both insulin and GPCR stimulated glucose uptake. In mTORC1, mTOR complexes with the regulatory-associated-protein of mTOR (Raptor), while in mTORC2, mTOR associates with the rapamycin-insensitive-companion of mTOR (Rictor). The latter complex is involved in phosphorylation of Akt on S473 (Alessi et al. 1997). It is known that rapamycin binds to newly synthesized mTOR and prevents it forming either complex (Sarbassov et al. 2004, Brown et al. 1994).

Figure 14:
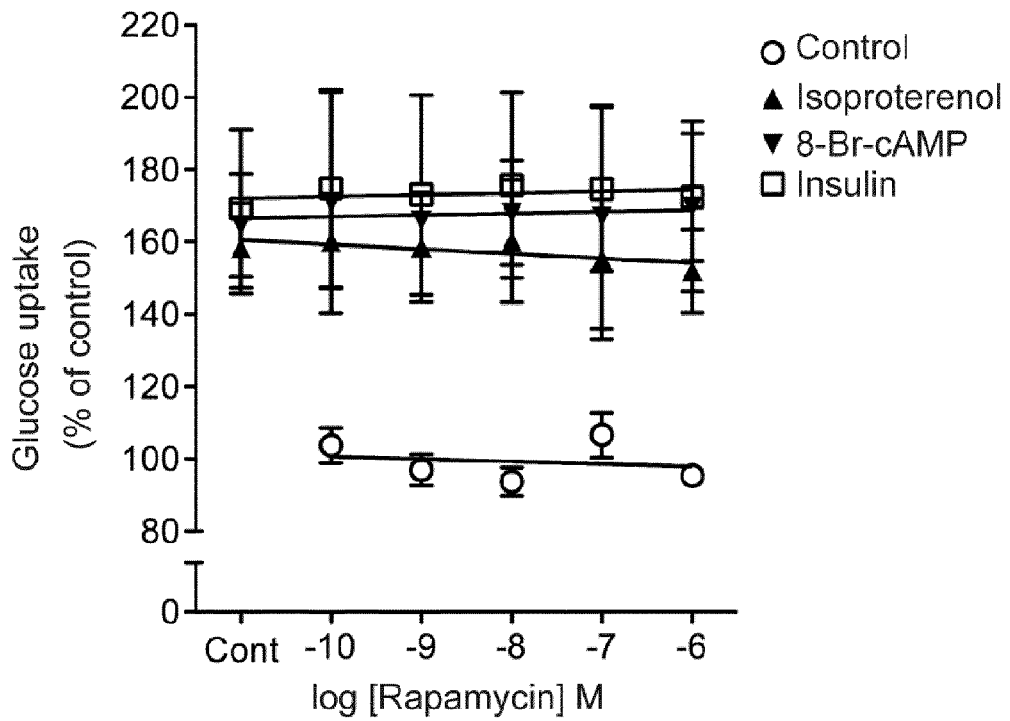
FIG. 14 is a semi-logarithmic graph showing glucose uptake (% of control) in L6 myotubes (control) and in L6 myotubes treated with isoproterenol, 8-Br-cAMP or insulin, respectively, and submitted to a short-term treatment with different concentrations of rapamycin.
Figure 15:
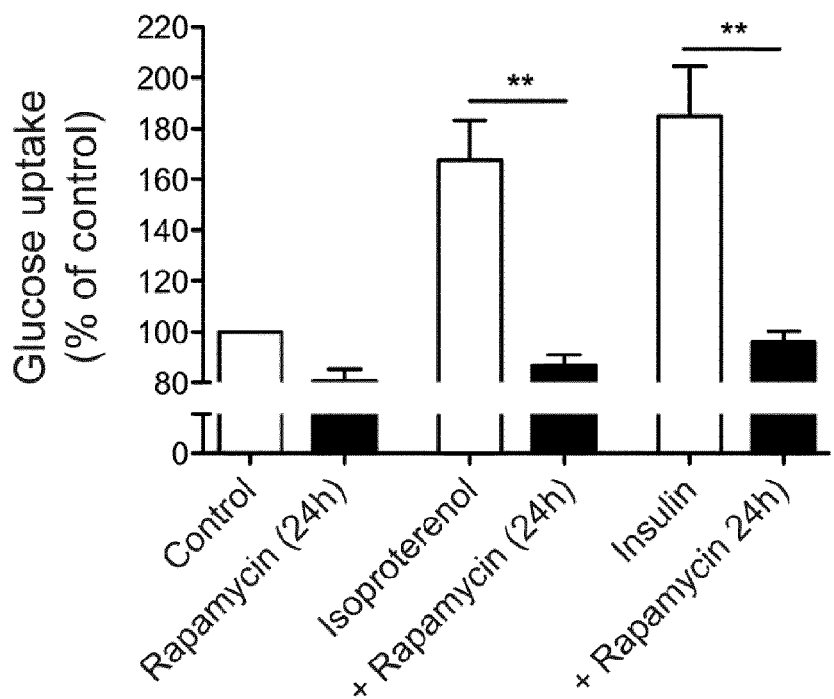
FIG. 15 is a bar chart showing glucose uptake (% of control) in L6 myotubes (control) and in L6 myotubes treated with isoproterenol or insulin, respectively, without any rapamycin treatment or with long-term treatment with rapamycin (+Rapamycin (24 h)).

To investigate the involvement of each mTOR complex in insulin or GPCR stimulated uptake, different times of pre-treatment with rapamycin were used. Short term treatment with rapamycin inhibits only mTORC1 whereas longer treatment also affects mTORC2. Short term treatment had no effect on either insulin mediated or isoproterenol mediated glucose uptake (FIG. 14), whereas prolonged treatment (72 h) with rapamycin abolished both insulin- and isoproterenol mediated glucose uptake (FIG. 15).

Next siRNA constructs directed against, rictor or raptor or scrambled siRNA controls were used. Myotubes were detached by trypsin/EDTA, transferred to Eppendorf tubes and centrifuged at 1000×g for 3 min, resuspended in 20 µl SE Cell Line Nucleofector solution for L6 cells and P1 primary Nucleofector solution for SKMC, with supplement (Lonza) and 100 pmol of siRNA (L6 myotubes) or 0.8 µg GLUT4mycGFP construct (L6 myoblasts and human SKMC) added. Cells were electroporated in 16-well microcuvette plates (Lonza) followed by 80 µl of pre-warmed RPMI1640, and then transferred to tubes containing DMEM with 10% FBS, 8 h later medium was changed to serum-free medium (0.1% BSA) and incubated overnight. 24 h after transfection, glucose uptake, immunohistochemistry or western blotting was performed as described above.

Figure 16:
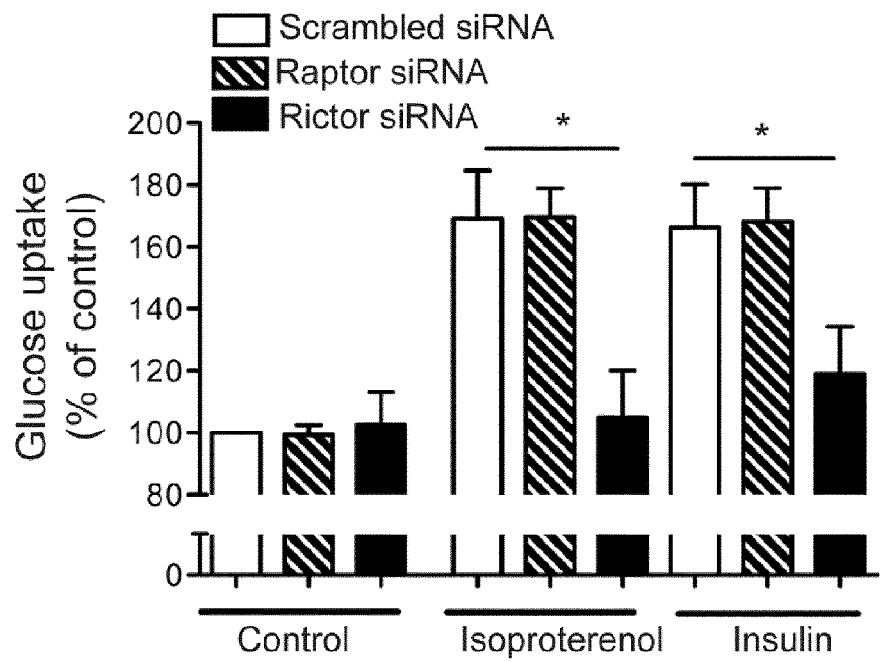
FIG. 16 is a bar chart showing glucose uptake (% of control) in L6 myotubes (control) and in L6 myotubes treated with isoproterenol or insulin, and transfected with scrambled siRNA, Raptor siRNA or Rictor siRNA, respectively.
Figure 17:
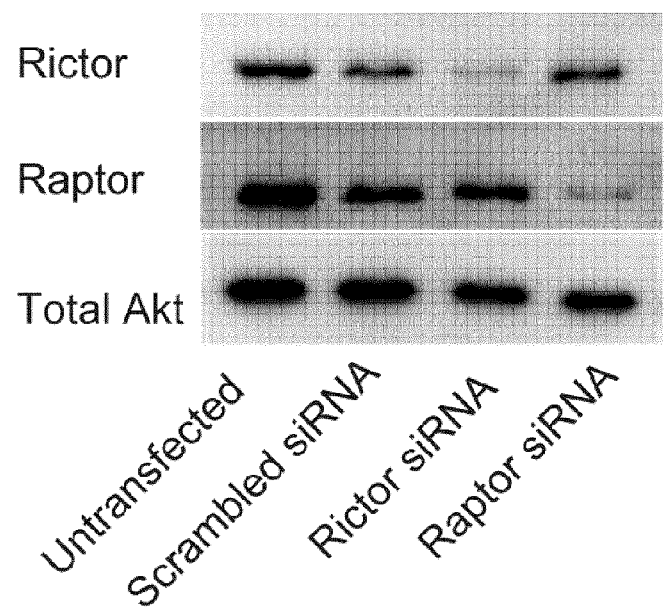
FIG. 17 is a western blot showing total Akt, Rictor and Raptor in L6 myotubes that were either untransfected or transfected with scrambled siRNA, Rictor siRNA or Raptor siRNA.
Figure 18:
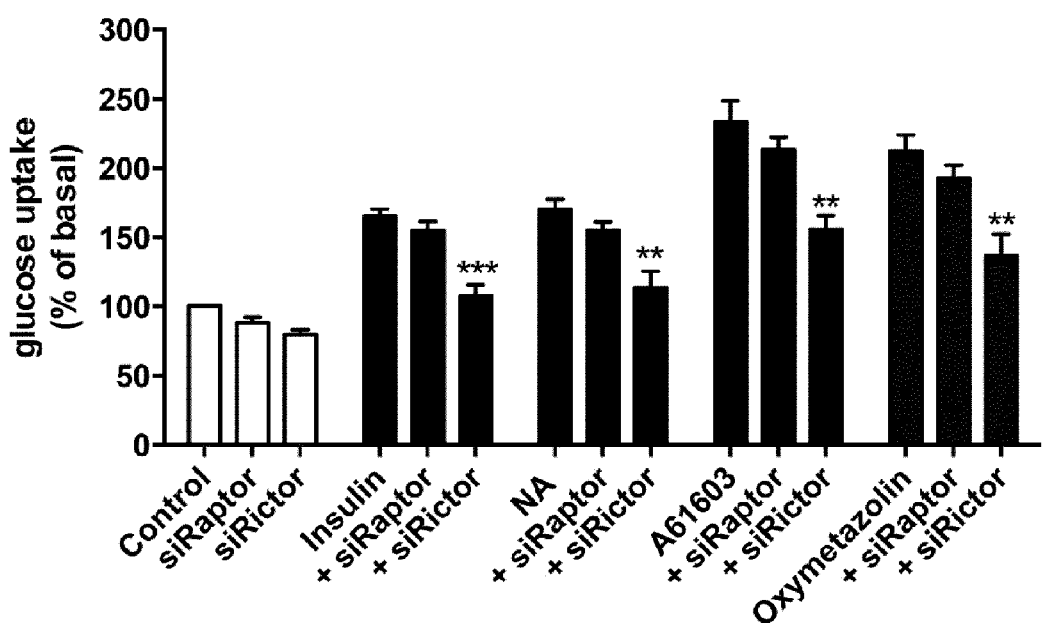
FIG. 18 is a bar chart showing glucose uptake (% of basal) in CHO GLUT4 (control) and in CHO GLUT4 treated with insulin, noradrenaline (NA), A61603, and oxymetazoline; and transfected with Raptor siRNA or Rictor siRNA, respectively.

Both control siRNA and efficient knock-down of Raptor failed to affect either insulin or GPCR-stimulated glucose uptake, whereas Rictor siRNA treatment markedly depleted Rictor protein and abolished both insulin- and GPCR-stimulated glucose-uptake in L6 (FIGS. 16-17) and CHO glut 4 (FIG. 18). This clearly demonstrates that mTORC2 is a key regulator of both insulin and GPCR stimulated glucose uptake in skeletal muscle and can thus be utilized to increase glucose uptake in peripheral tissues.

Taken together, we show that mTORC2 exerts the same function according to both anabolic and catabolic upstream stimuli; in response to insulin pathway activation, mTORC2 acts via one Akt-dependent and one Akt-independent mechanism whereas $\beta_2$-AR activation utilizes only the Akt independent mechanism. Both insulin, acting anabolically, and adrenergic stimulation, acting catabolically, increase glucose uptake in skeletal muscle with mTORC2 being a common factor.

Anabolic processes activated through Akt and mTORC1 such as transcription, translation and other processes influence many proteins that could have negative impact on type 2 diabetes. It would therefore beneficial to be able to stimulate mTORC2 without stimulation of Akt and mTORC1.

The mTORC2 pathway that is independent of Akt can thus be utilized to achieve glucose uptake in peripheral tissues without activating unwanted processes and without side effects that are linked to Akt activity.

Example 4

Figure 19:
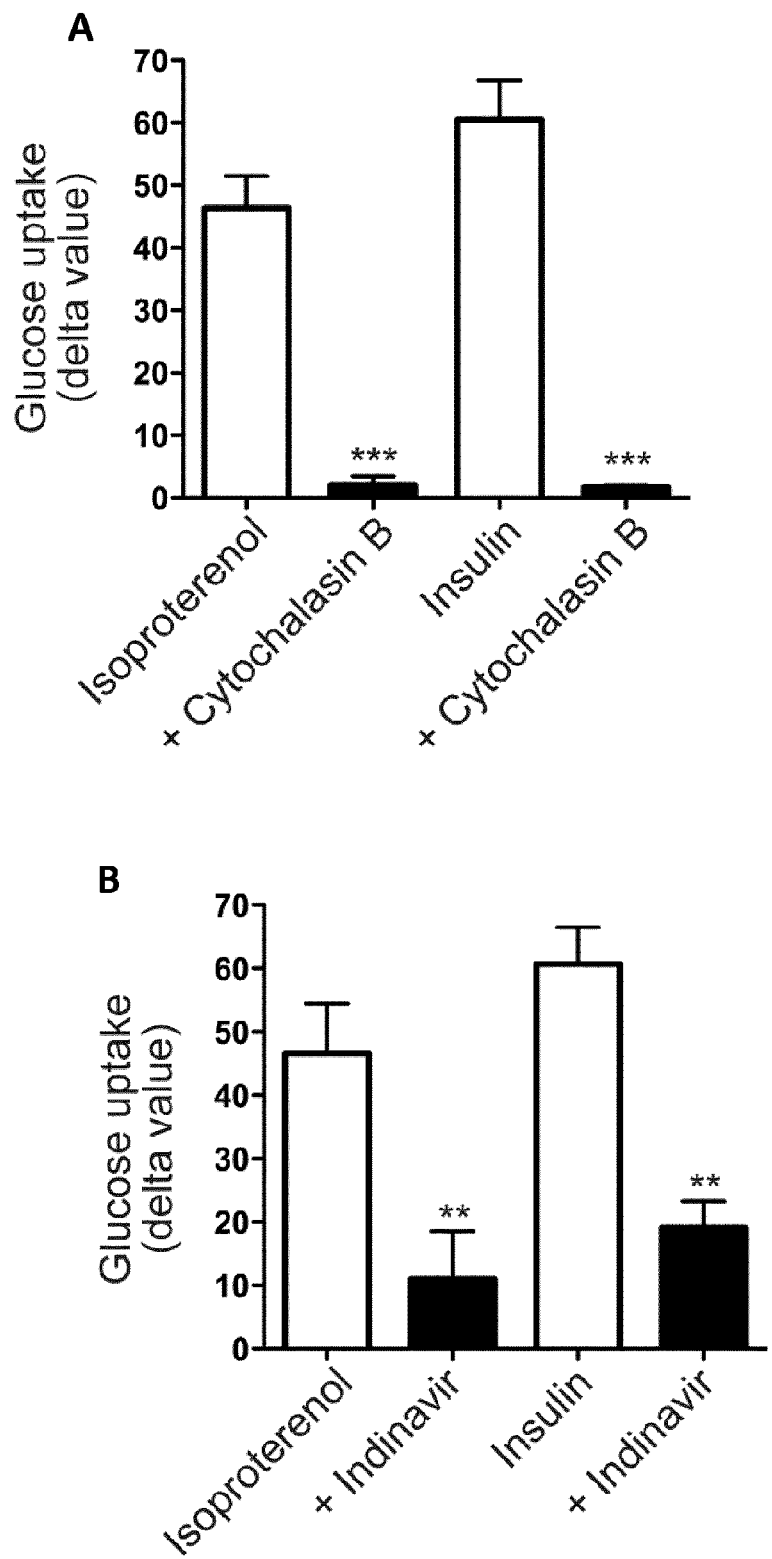
FIG. 19 is (A) a bar chart showing glucose uptake (delta value) in L6 myotubes treated with isoproterenol and insulin and in L6 myotubes treated with isoproterenol and insulin as well as with the GLUT inhibitor cytochalasin B (+Cytochalasin B); and (B) a bar chart showing glucose uptake (delta value) in L6 myotubes treated with isoproterenol and insulin and in L6 myotubes treated with isoproterenol and insulin as well as with the GLUT4 inhibitor indinavir (+Indinavir).
Figure 20:
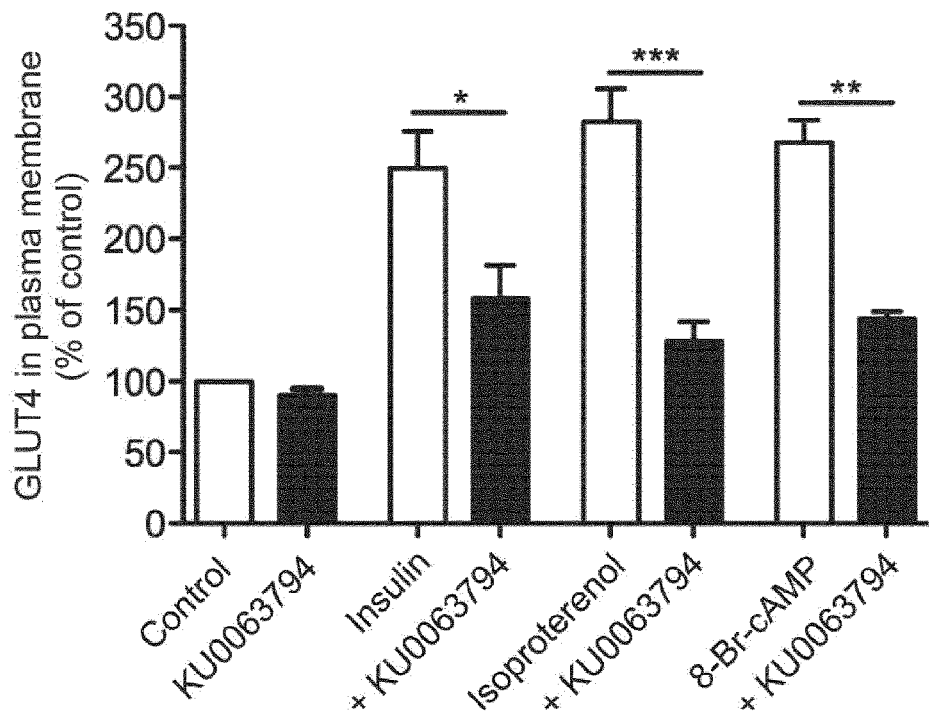
FIG. 20 is a bar chart showing amount of GLUT4 in plasma membrane as a percentage of the amount of GLUT4 in plasma membrane of control cells ((% of control), in L6 myotubes (control) and in L6 myotubes treated with insulin, isoproterenol or 8-Br-cAMP, in the absence or presence (+KU0063794) of the mTOR inhibitor KU0063794.

Glucose uptake can be increased by de novo synthesis of GLUTs associated with increases in transcription and/or translation. Both the GLUT inhibitor cytochalasin B (10 µM) and the selective GLUT4 inhibitor indinavir (100 µM), blocked basal glucose uptake by ~40% (FIG. 19) and markedly reduced GPCR and insulin-stimulated glucose uptake, which suggests a role for GLUTs. The GLUT4 translocation in response to GPCR stimulation was abolished by mTOR inhibition (FIG. 20).

Example 5

Figure 21:
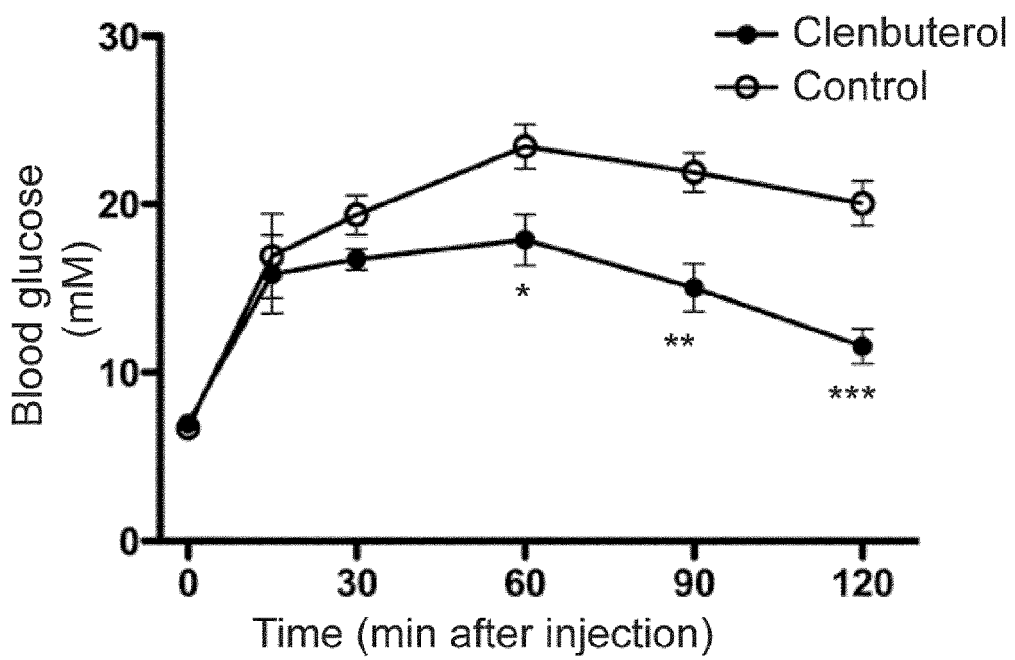
FIG. 21 is a graph showing blood glucose (mM) in untreated GK-rats or in rats treated with Clenbuterol, as a function of time after injection of glucose into the rats.

Goto-Kakizaki GK-rats, showing impaired glucose tolerance form an established model of type 2 diabetes. GK-rats were split into two groups, one of which was treated with the GPCR agonist clenbuterol in the drinking water for 4 days prior to a glucose tolerance test. GPCR-agonist treated GK-rats had greatly improved blood glucose levels after 60, 90 and 120 minutes compared to untreated animals (FIG. 21), which demonstrates that GPCR stimulation greatly reduces symptoms of type 2 diabetes.

Taken together, the examples further illustrate that the screening method according to the invention allows for the identification of a compound for the treatment of a condition involving a dysregulation of metabolism, e.g. glucose homeostasis or glucose uptake in a mammal.

Example 6

The above described experiments together also illustrate the screening method of the invention. Thus, in the Examples, a compound was brought into contact with CHO GLUT4 cells, L6 myoblasts and L6 myotubes. The compound was selected from insulin, isoproterenol, noradrenaline, A61603 and oxymetazoline. The mTORC2 activity in cells brought into contact with the compound was determined Here, the mTORC2 activity was represented by glucose uptake (FIGS. 1 and 2), or by the mTOR phosphorylation (FIG. 13), or by translocation of GLUT4 (FIG. 20). Further, the Akt activity in cells brought into contact with the compound was determined. Here Akt activity was represented by phosphorylation of Akt (FIG. 5 and FIG. 6), or phosphorylation of a target molecule downstream of Akt, here AS160 (FIG. 7).

Table 1 shows schematically the effect on mTORC2 activities and Akt activities determined for the different compounds. In Table 1, the numbers within brackets refer to the relevant Figures of the drawings. The sign "+" indicates that an increase of the activity was determined, compared to a reference, whereas the sign "−" indicates that no significant increase of the activity was determined compared to a reference (a significant activity may be estimated e.g. using any of the above ratios r, r' or r"). The reference was cells that had not been brought into contact with the compound.

TABLE 1

| Compound | mTORC2 activity represented by | | | Akt activity represented by | |
|---|---|---|---|---|---|
| | phosphorylation of mTORC2 | glucose uptake | GLUT translocation | phosphorylation of Akt | phophorylation of Akt substrate |
| insulin | +(13) | +(2) | +(20) | +(5, 6) | +(7) |
| isoproterenol | +(13) | +(1, 2) | +(20) | −(5) | −(7) |
| noradrenaline | n.d. | +(1) | n.d. | −(6) | n.d. |
| A61603 | n.d. | +(1) | n.d. | −(6) | n.d. |
| oxymetazoline | n.d. | +(1) | n.d. | −(6) | n.d. |

Based on the entries in Table 1, isoproterenol, noradrenaline, A61603, oxymetazoline are identified as candidate compounds according to the screening method of the present invention.

Example 7

In Example 6, insulin and isoproterenol were both referred to as compounds to be screened as possible candidate compounds. However, as noted herein above, insulin may also be used as a reference in determining Akt activity.

Using approximate Akt Activity values indicated in FIG. 6B, and insulin to determine a value of $Akt_{agonist}$, ratios r, r' and r" were calculated and are shown in Table 2:

TABLE 2

| Compound | Akt p-S473 % basal | r | r' | r" |
|---|---|---|---|---|
| — | 100 | 0 | 1 | 0 |
| insulin | 170 | 0.7 | 0 | 1 |
| noradrenaline | 130 | 0.3 | 0.2 | 0.4 |
| A61603 | 135 | 0.35 | 0.2 | 0.5 |
| oxymetazoline | 135 | 0.35 | 0.2 | 0.5 |

While this invention has been described with respect to various specific examples it is to be understood that the invention is not limited by this and it can be variously practiced within the scope of the general claim.

REFERENCE LIST

Alessi, D. R., James, S. R., Downes, C. P., Holmes, A. B., Gaffney, P. R., Reese, C. B. & Cohen, P. 1997, "Characterization of a 3-phosphoinositide-dependent protein kinase which phosphorylates and activates protein kinase Balpha", Current biology: CB, vol. 7, no. 4, pp. 261-269.

Barnes, K., Ingram, J. C., Porras, O. H., Barros, L. F., Hudson, E. R., Fryer, L. G., Foufelle, F., Carling, D., Hardie, D. G. & Baldwin, S. A. 2002, "Activation of GLUT1 by metabolic and osmotic stress: potential involvement of AMP-activated protein kinase (AMPK)", Journal of cell science, vol. 115, no. Pt 11, pp. 2433-2442.

Brown, E. J., Albers, M. W., Shin, T. B., Ichikawa, K., Keith, C. T., Lane, W. S. & Schreiber, S. L. 1994, "A mammalian protein targeted by G1-arresting rapamycin-receptor complex", Nature, vol. 369, no. 6483, pp. 756-758.

Carayannopoulos, M. O., Chi, M. M., Cui, Y., Pingsterhaus, J. M., McKnight, R. A., Mueckler, M., Devaskar, S. U. & Moley, K. H. 2000, "GLUT8 is a glucose transporter responsible for insulin-stimulated glucose uptake in the blastocyst", Proceedings of the National Academy of Sciences of the United States of America, vol. 97, no. 13, pp. 7313-7318.

Copp, J., Manning, G. & Hunter, T. 2009, "TORC-specific phosphorylation of mammalian target of rapamycin (mTOR): phospho-Ser2481 is a marker for intact mTOR signaling complex 2", Cancer research, vol. 69, no. 5, pp. 1821-1827.

Dehvari, N., Hutchinson, D. S., Nevzorova, J., Dallner, O. S., Sato, M., Kocan, M., Merlin, J., Evans, B. A., Summers, R. J. & Bengtsson, T. 2011, "beta(2)-Adrenoceptors increase translocation of GLUT4 via G protein-coupled receptor kinase sites in the receptor C-terminal tail", British journal of pharmacology.

Drake, M. T., Shenoy, S. K. & Lefkowitz, R. J. 2006, "Trafficking of G protein-coupled receptors", Circulation research, vol. 99, no. 6, pp. 570-582.

Garcia-Martinez, J. M., Moran, J., Clarke, R. G., Gray, A., Cosulich, S. C., Chresta, C. M. & Alessi, D. R. 2009, "Ku-0063794 is a specific inhibitor of the mammalian target of rapamycin (mTOR)", The Biochemical journal, vol. 421, no. 1, pp. 29-42.

Gawlik, V., Schmidt, S., Scheepers, A., Wennemuth, G., Augustin, R., Aumuller, G., Moser, M., Al-Hasani, H., Kluge, R., Joost, H. G. & Schurmann, A. 2008, "Targeted disruption of Slc2a8 (GLUT8) reduces motility and mitochondrial potential of spermatozoa", Molecular membrane biology, vol. 25, no. 3, pp. 224-235.

Harrison, S. A., Clancy, B. M., Pessino, A. & Czech, M. P. 1992, "Activation of cell surface glucose transporters measured by photoaffinity labeling of insulin-sensitive 3T3-L1 adipocytes", Journal of Biological Chemistry, vol. 267, no. 6, pp. 3783-3788.

Hawkins, P. T., Anderson, K. E., Davidson, K. & Stephens, L. R. 2006, "Signalling through Class I PI3Ks in mammalian cells", Biochemical Society transactions, vol. 34, no. Pt 5, pp. 647-662.

Hebert, D. N. & Carruthers, A. 1986, "Direct evidence for ATP modulation of sugar transport in human erythrocyte ghosts", The Journal of biological chemistry, vol. 261, no. 22, pp. 10093-10099.

Hresko, R. C. & Mueckler, M. 2005, "mTOR.RICTOR is the Ser473 kinase for Akt/protein kinase B in 3T3-L1 adipocytes", The Journal of biological chemistry, vol. 280, no. 49, pp. 40406-40416.

Koshy, S., Alizadeh, P., Timchenko, L. T. & Beeton, C. 2010, "Quantitative measurement of GLUT4 translocation to the plasma membrane by flow cytometry", Journal of visualized experiments: JoVE, vol. (45). pii: 2429. doi, no. 45, pp. 10.3791/2429.

Liggett, S. B., Shah, S. D. & Cryer, P. E. 1988, "Characterization of beta-adrenergic receptors of human skeletal muscle obtained by needle biopsy", The American Journal of Physiology, vol. 254, no. 6 Pt 1, pp. E795-8.

Nave, B. T., Ouwens, M., Withers, D. J., Alessi, D. R. & Shepherd, P. R. 1999, "Mammalian target of rapamycin is a direct target for protein kinase B: identification of a convergence point for opposing effects of insulin and amino-acid deficiency on protein translation", *The Biochemical journal*, vol. 344 Pt 2, pp. 427-431.

Nevzorova, J., Bengtsson, T., Evans, B. A. & Summers, R. J. 2002, "Characterization of the beta-adrenoceptor subtype involved in mediation of glucose transport in L6 cells", *British journal of pharmacology*, vol. 137, no. 1, pp. 9-18.

Nevzorova, J., Evans, B. A., Bengtsson, T. & Summers, R. J. 2006, "Multiple signalling pathways involved in beta2-adrenoceptor-mediated glucose uptake in rat skeletal muscle cells", *British journal of pharmacology*, vol. 147, no. 4, pp. 446-454.

Palmada, M., Boehmer, C., Akel, A., Rajamanickam, J., Jeyaraj, S., Keller, K. & Lang, F. 2006, "SGK1 kinase upregulates GLUT1 activity and plasma membrane expression", *Diabetes*, vol. 55, no. 2, pp. 421-427.

Rodnick, K. J., Piper, R. C., Slot, J. W. & James, D. E. 1992, "Interaction of insulin and exercise on glucose transport in muscle", *Diabetes care*, vol. 15, no. 11, pp. 1679-1689.

Rowland, A. F., Fazakerley, D. J. & James, D. E. 2011, "Mapping insulin/GLUT4 circuitry", *Traffic (Copenhagen, Denmark)*, vol. 12, no. 6, pp. 672-681.

Santulli, G. & Iaccarino, G. 2013, "Pinpointing beta adrenergic receptor in ageing pathophysiology: victim or executioner? Evidence from crime scenes", *Immunity & ageing: I & A*, vol. 10, no. 1, pp. 10-4933-10-10.

Sarbassov, D. D., Ali, S. M., Kim, D. H., Guertin, D. A., Latek, R. R., Erdjument-Bromage, H., Tempst, P. & Sabatini, D. M. 2004, "Rictor, a novel binding partner of mTOR, defines a rapamycin-insensitive and raptor-independent pathway that regulates the cytoskeleton", *Current biology: CB*, vol. 14, no. 14, pp. 1296-1302.

Sekulic, A., Hudson, C. C., Homme, J. L., Yin, P., Otterness, D. M., Karnitz, L. M. & Abraham, R. T. 2000, "A direct linkage between the phosphoinositide 3-kinase-AKT signaling pathway and the mammalian target of rapamycin in mitogen-stimulated and transformed cells", *Cancer research*, vol. 60, no. 13, pp. 3504-3513.

Shah, K., Desilva, S. & Abbruscato, T. 2012, "The Role of Glucose Transporters in Brain Disease: Diabetes and Alzheimer's Disease", *International journal of molecular sciences*, vol. 13, no. 10, pp. 12629-12655.

Simpson, I. A., Dwyer, D., Malide, D., Moley, K. H., Travis, A. & Vannucci, S. J. 2008, "The facilitative glucose transporter GLUT3: 20 years of distinction", *American journal of physiology. Endocrinology and metabolism*, vol. 295, no. 2, pp. E242-53.

Taha, C., Mitsumoto, Y., Liu, Z., Skolnik, E. Y. & Klip, A. 1995, "The insulin-dependent biosynthesis of GLUT1 and GLUT3 glucose transporters in L6 muscle cells is mediated by distinct pathways. Roles of p21ras and pp70 S6 kinase", *The Journal of biological chemistry*, vol. 270, no. 42, pp. 24678-24681.

Watson-Wright, W. M. & Wilkinson, M. 1986, "The muscle slice—a new preparation for the characterization of beta-adrenergic binding in fast- and slow-twitch skeletal muscle", *Muscle & nerve*, vol. 9, no. 5, pp. 416-422.

The invention claimed is:

1. A method of screening for a candidate compound for the treatment of a condition involving dysregulation of metabolism in a mammal, said method comprising:
   bringing a compound into contact with at least one population of cells, comprising cells that express mTOR and Akt and that are capable of activating mTORC2 and Akt;
   determining mTORC2 activity and Akt activity in the cells brought into contact with the compound;
   selecting the compound as a candidate compound, if the compound causes an increase in activity of mTORC2 but does not cause an increase in activity of Akt, and
   testing the candidate compound in pharmacological, clinical and/or toxicological tests.

2. The method of claim 1, wherein the cells are mammalian cells.

3. The method of claim 2, wherein the mammalian cells are muscle cells.

4. The method of claim 1, wherein the activity of mTORC2 in the cells is determined by measuring phosphorylation of mTOR; or where the activity of Akt in the cells is determined by measuring phosphorylation of Akt.

5. The method of claim 1, wherein the candidate compound is identified by comparison with mTORC2 and Akt activities determined in cells that have not been brought into contact with the compound.

6. The method of claim 1, wherein the condition involving a dysregulation of metabolism in a mammal is a condition involving a dysregulation of glucose homeostasis or glucose uptake.

7. The method of claim 1, wherein the condition involving a dysregulation of metabolism in a mammal is selected from the group consisting of Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, and vascular disease.

8. The method of claim 7, wherein the condition involving a dysregulation of metabolism in a mammal is diabetes.

\* \* \* \* \*